US009549837B2

(12) United States Patent
Summit et al.

(10) Patent No.: US 9,549,837 B2
(45) Date of Patent: Jan. 24, 2017

(54) BRACE WITH ELONGATED FENESTRATIONS

(71) Applicant: 3D Systems, Inc., Rock Hill, SC (US)

(72) Inventors: Scott Summit, Mill Valley, CA (US); Kenneth B Trauner, San Francisco, CA (US)

(73) Assignee: 3D Systems, Inc., Rock Hill, SC (US)

( * ) Notice: Subject to any disclaimer, the term of this patent is extended or adjusted under 35 U.S.C. 154(b) by 146 days.

(21) Appl. No.: 13/761,004

(22) Filed: Feb. 6, 2013

(65) Prior Publication Data

US 2013/0150762 A1 Jun. 13, 2013

Related U.S. Application Data

(63) Continuation-in-part of application No. PCT/US2012/051612, filed on Aug. 20, 2012, which is a continuation-in-part of application No. 13/214,096, filed on Aug. 19, 2011, now abandoned, which is a continuation-in-part of application No. 12/820,968, filed on Jun. 22, 2010, now abandoned, which is a continuation-in-part of application No. 12/615,196, filed on Nov. 9, 2009, now Pat. No. 8,005,651.

(Continued)

(51) Int. Cl.
*A61F 5/01* (2006.01)
*A61F 5/02* (2006.01)
*A61F 5/058* (2006.01)

(52) U.S. Cl.
CPC ............... *A61F 5/013* (2013.01); *A61F 5/01* (2013.01); *A61F 5/0123* (2013.01); *A61F 5/02* (2013.01); *A61F 5/05841* (2013.01); *A61F 5/05866* (2013.01)

(58) Field of Classification Search
CPC A61F 5/05841; A61F 5/0585; A61F 5/05858; A61F 5/05866; A61F 5/05825; A61F 13/04; A61F 13/046; A61L 5/07
USPC .................................................. 602/6–8, 21
See application file for complete search history.

(56) References Cited

U.S. PATENT DOCUMENTS 2,980,110 A * 4/1961 Brumfield et al. ............... 602/5
4,294,240 A * 10/1981 Thill ..................... A61F 13/041 602/21

(Continued)

FOREIGN PATENT DOCUMENTS

DE 811256 8/1951
GB 821959 10/1959

(Continued)

OTHER PUBLICATIONS

PCT International Search Report and Written Opinion of the International Searching Authority.

(Continued)

*Primary Examiner* — Kari Petrik

(57) ABSTRACT

A brace has a plurality of elongated beams that extend in parallel along the length of the brace. The adjacent beams are coupled to posts that extend around the circumference of the brace in a staggered pattern and hold the beams in place around the brace. The beams and posts define a plurality of elongated fenestrations. The configuration of the beams and fenestrations allow the brace to be strong in compression and bending and also provide elastic radial expansion.

22 Claims, 25 Drawing Sheets

Related U.S. Application Data

(60) Provisional application No. 61/720,878, filed on Oct. 31, 2012, provisional application No. 61/720,861, filed on Oct. 31, 2012, provisional application No. 61/596,037, filed on Feb. 7, 2012, provisional application No. 61/112,751, filed on Nov. 9, 2008, provisional application No. 61/168,183, filed on Apr. 9, 2009, provisional application No. 61/185,781, filed on Jun. 10, 2009.

(56) References Cited

U.S. PATENT DOCUMENTS

| | | | |
|---|---|---|---|
| 5,160,314 | A | 11/1992 | Peters |
| 5,695,453 | A | 12/1997 | Neal |
| 5,836,902 | A | 11/1998 | Gray |
| 6,942,628 | B1 * | 9/2005 | Watson ............ 602/8 |
| 7,749,181 | B2 | 7/2010 | Simmons et al. |
| 7,985,192 | B2 | 7/2011 | Sheehan et al. |
| 2006/0084333 | A1 | 4/2006 | Watson |
| 2008/0154164 | A1 * | 6/2008 | Sheehan et al. ............ 602/7 |
| 2008/0249443 | A1 | 10/2008 | Avitable |
| 2008/0319362 | A1 | 12/2008 | Joseph |
| 2010/0262054 | A1 | 10/2010 | Summit et al. |

FOREIGN PATENT DOCUMENTS

| | | |
|---|---|---|
| JP | 2007-500586 | 1/2007 |
| JP | 2008-512170 | 4/2008 |
| WO | WO 01/01902 | 1/2001 |
| WO | 2006027763 | 3/2006 |

OTHER PUBLICATIONS

Extended European Search Report for European Patent Application 13746644.7, dated Dec. 22, 2015 (7 pages).

Japan's First Action for Japan Patent Application No. 2014-556642, dated Oct. 23, 2015 (3 pages).

Japan's Final Office Action for Japan Patent Application No. 2014-556642, dated Apr. 5, 2016 (3 pages).

* cited by examiner

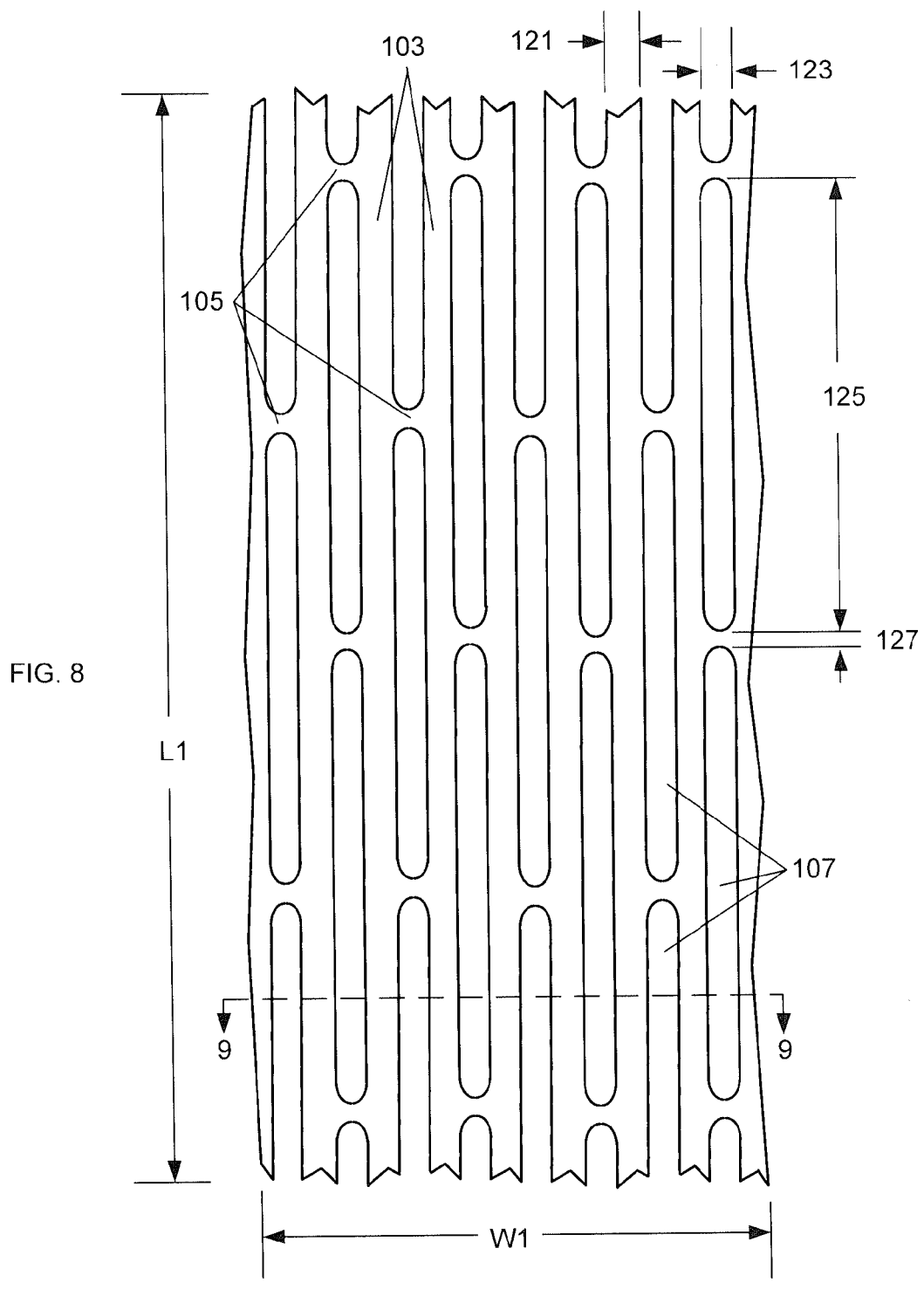

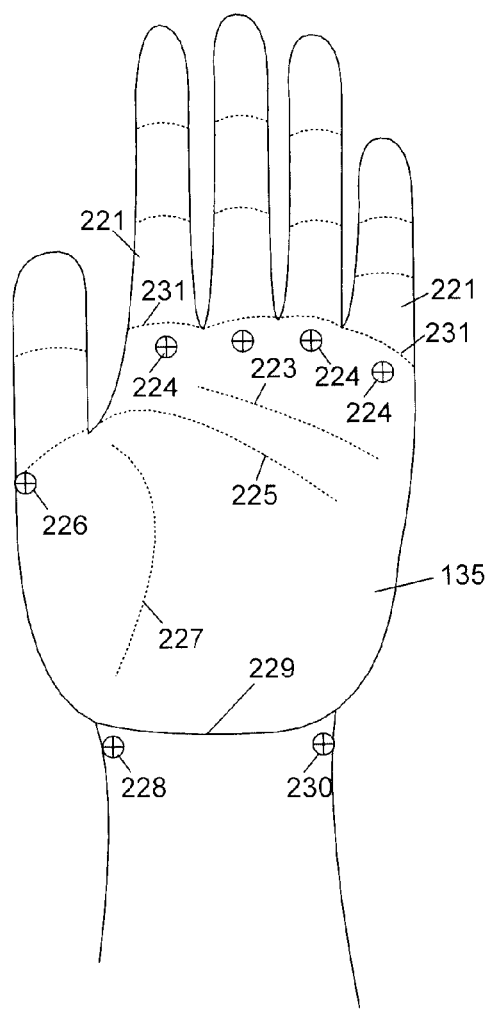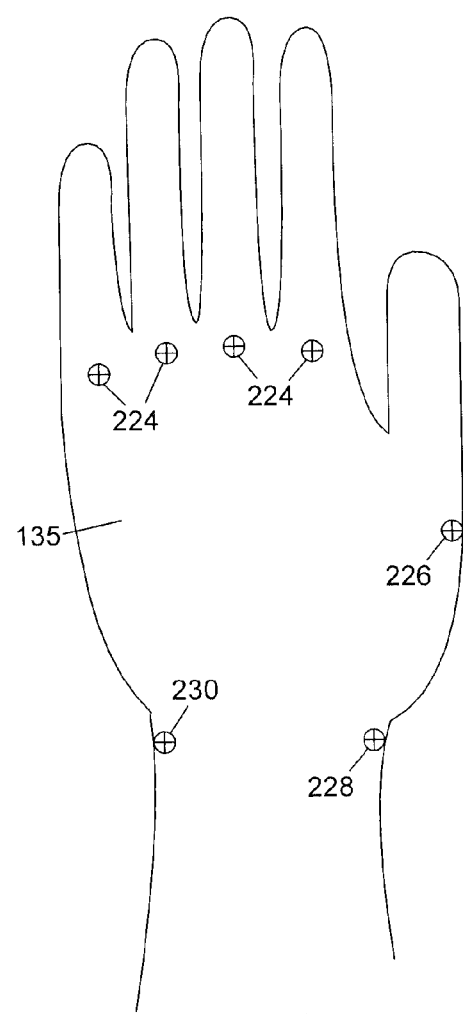
FIG. 39
FIG. 40

BRACE WITH ELONGATED FENESTRATIONS

CROSS REFERENCE TO RELATED APPLICATIONS

This application claims priority to U.S. Provisional Application No. 61/720,878, "Bikini Brace" filed Oct. 31, 2012, U.S. Provisional Application No. 61/720,861, "Spiral Brace" filed Oct. 31, 2012 and U.S. Provisional Application No. 61/596,037, "Fracture Brace" filed Feb. 7, 2012 and is a continuation-in-part of PCT Patent Application. No. PCT/US2012/051612, "Adjustable Brace" filed Aug. 20, 2012 which claims priority to U.S. patent application Ser. No. 13/214,096, "Adjustable Brace" filed Aug. 19, 2011 which is a continuation-in-part of U.S. patent application Ser. No. 12/820,968, "Modular Custom Braces, Casts And Devices And Methods For Designing And Fabricating filed Jun. 22, 2010 which is a continuation-in-part of U.S. patent application Ser. No. 12/615,196, now U.S. Pat. No. 8,005,651, "Custom Braces, Casts and Devices And Methods For Designing And Fabricating" filed Nov. 9, 2009 which claims priority to U.S. Provisional Patent Application No. 61/112,751, "Brace And Cast" filed on Nov. 9, 2008, U.S. Provisional Patent Application No. 61/168,183, "Orthopedic Braces" filed in Apr. 9, 2009, and U.S. Provisional Patent Application No. 61/185,781, "Bespoke Fracture Brace" filed in Jun. 10, 2009. The contents of PCT Application No. PCT/US2012/051612 and U.S. Patent Application Nos. 61/720,878, 61/720,861, 61/596,037, Ser. Nos. 13/214,096, 12/820,968, 12/615,196, 61/112,751, 61/168,183, and 61/185,781 are hereby incorporated by reference.

BACKGROUND

A problem with braces is that they can be complicated to secure to the patient's body, uncomfortable to wear and unattractive to look at. Many braces have thick padding that is placed around the injured limb and a rigid structure around the padding that prevents the brace from moving which immobilizes the limb. Because of these issues, many patients tend to not wear braces that have been fitted to the patients by their physicians. What is needed is an improved and simplified brace that is easily placed on the patient's body, comfortable to wear and more attractive than existing braces.

SUMMARY OF THE INVENTION

The present invention is directed towards a brace that has a fenestrated structure that surrounds an injured limb to prevent or restrict movement of the limb. The brace has elongated fenestrations that can extend along the length of the brace. The elongated fenestrations can be substantially parallel to each other and the adjacent fenestrations can be separated by beams that also extend along the length of the brace. The adjacent beams can be coupled to each other by posts which can be substantially shorter than the beams and may be substantially perpendicular to the beams. Thus, each fenestration can have sides defined by two beams and ends defined by two posts. The adjacent fenestrations can be offset along the length of the brace so that the ends of a fenestration and posts can be coupled close to the mid sections of the adjacent fenestrations. By connecting the adjacent beams with posts at the ends and mid section of each beam, the brace can be selectively flexible. In an embodiment, the brace can be elastic and expand radially. However, the brace can also be strong in length and resist axial compression and bending about an axis perpendicular to the length. The fenestrations also allow air to circulate around the portions of the limb covered by the beams and posts.

The brace can be flexible in response to radial forces within the brace. More specifically, the inventive brace can be radially elastic and may deform to accommodate swelling of the limb or protrusions from the limb. This radial elasticity can be particularly useful when the cross section of the patient's limb changes over time. For example, with a traditional rigid brace or case, the interior cross section can be a proper fit for the injured swollen limb. However, as the limb heals and atrophies, the cross section of the limb will decrease. Because the brace is a completely rigid structure a large gap between the limb and the brace can form and the brace may lose it ability to properly support the limb as it heals and is in a weakened state. The brace may eventually need to be replaced.

In contrast, the inventive brace can expand radially and may elastically stretch to fit over an enlarged portion of an injured limb. As the limb heals and any swelling or inflammation decreases, the cross section of the brace can shrink with the surface of the limb. Thus, the brace can continue to provide a close fit over the limb and proper support for the patient's limb. This flexibility can be beneficial because the inventive brace may not need to be changed even when the size and cross section of the patient's limb has changed.

In an embodiment, a seam may extend along the length of the brace which allows the brace to be opened to that the limb can be easily placed in the brace. The fenestrations may also allow the brace to be flexible in radial bending to that it can be opened easily. This radial bending motion can include torsion rotation of the beams along the elongated portions between the posts and the ends of the fenestrations. Once the brace is properly positioned on the limb, the brace can be closed along the seam and one or more fasteners may be used to secure the edges of the seam together to secure the brace around the limb. In other embodiments, the brace may not include a seam and the user may slide the brace over the limb like a sleeve until it is properly positioned on the patient's body. The cross sections of the brace can expand and contract as the brace is pulled over the limb.

The brace may allow axial twisting or axial rotation of the limb, but may prevent bending movements of the limb. For example, if the brace is an arm brace, it may allow rotation about a center axis of the brace relative to the forearm such as axial rotation of the hand for movements such as rotating door knobs. However, the brace may also prevent bending of the wrist such as palmar flexion movement of the hand.

There are various features that make the brace comfortable to wear. Because the brace is thin it can be easily worn under clothing. The brace is also light weight and fenestrated to allow the limb to be exposed to ambient air so that perspiration from the limb can evaporate rather than being trapped by the brace. A brace can have thickness that is between about 0.05 inch and 0.50 inch and may weigh between about 0.2 lbs. to 3 lbs. Because the brace can be made very thin and light weight, the patient is more likely to wear the inventive brace.

In an embodiment, the brace can be used as an arm brace. The brace can have a proximal portion that fits around a forearm portion of the limb and a distal portion of the brace body fits around a hand portion of the limb. The distal portion of the brace can fit against the palm and dorsum to prevent or limit movement of the hand. Because the brace can be radially elastic, the inner surfaces of the brace can provide a very close fit that can keep the brace in proper alignment with the arm. Because the surface of the palm of the hand is normally concave, the inner surface of the brace body at the palmar distal portion includes a convex surface that corresponds to the concave surface of the palm.

The brace can also be configured to provide specific types of support for the hand. For example, in an embodiment, the distal edge of the brace may also not extend over proximal phalanx segments of the fingers so that the movement of fingers may be restricted but not completely prevented. In an embodiment, the distal limb support of the brace does not extend over a thenar portion of the hand allowing a thumb of the hand to move freely. By knowing the type of hand injury, a proper brace design can be selected to prevent or restrict movement that can provide the best rehabilitation or therapy for the limb. The brace can also be designed to allow other movement of the hand to improve comfort and allow as must hand mobility as possible.

If the brace is being used to prevent movement of the wrist to prevent carpal tunnel injury, the brace can include structural members around the arm that will prevent wrist movement. For example, the brace can include a distal limb support that is adjacent to a palmar surface of the hand, a middle section that includes a plurality of elongated beams that extend along the length of the brace and a proximal limb support that fully or partially surrounds a portion of the forearm. If the patient attempts to move the palm in a downward motion about the wrist, the downward force will be resisted by the middle section and the proximal section. Although the brace can allow some movement, the brace functions to resist wrist movement to prevent injuries such as median nerve entrapment or carpal tunnel syndrome.

In an embodiment, the inventive brace can be a generic brace that can be an off the shelf stock item at a doctor's office, a hospital or a medical supply store. The inventive brace may be available in a variety of sizes and designs so that an optimal brace providing the best fit can be selected based upon the patient's anatomy and injury. In an embodiment, one or more portions of the injured limb can be measured and a brace can be selected that provides the best fit for the patient. For example, in an embodiment, the brace can be an arm brace. The most critical portion of the brace can be the hand fit. Thus, some anatomical features of the patient's hand such as finger knuckles, thumb knuckle, radial styloid, and the ulnar styloid can be measured and the best fitting brace size can be selected for the patient based upon these measurements.

In another embodiment, the inventive brace can be a custom product that is designed for a specific patient's limb and injury. In order to design a custom brace, a digital representation of the injured limb may first be obtained through a plurality of photographs. One or more colored stickers can be applied to the patient's limb and a plurality of markings or points of visible or IR light can be projected to the patient's limb. The light sources can project a pattern of light spots onto the limb. The limb can be placed on a positioning stand between a plurality of infrared (IR) and/or visible light cameras. A doctor may mark the injured areas of the limb with a pen, stickers or any other suitable marker that provide a suitable contrast to the skin of the patient. Some of the markings can be used for position detection. Markings can also indicate the areas where the patient is injured such as bone breakage, or swollen areas, etc. Other markings can indicate desired an edge or a seam of the brace. These markings can be captured by the digital photographic images and the marking locations can be used to design the adjustable brace. From the photographs, a three dimensional digital representation of the limb can be created by photogrammetry, image correlation, depth mapping or any other suitable IR and/or visible light photography based surface topography detection method. From the three dimensional representation of the limb surface topography, a brace can be designed having an inner surface that corresponds to the three dimensional digital representation of the patient's limb.

In an embodiment, the brace conforms to the surface of the patient's limb and can be worn by the patient without any compressible padding. The brace can be made of a hard plastic material and the inner surface of the brace should also be very smooth. In order to be comfortable, the inner surface can have a surface finish of less than of less than 500 $R_a$ μ inch. A brace or cast that can be worn by a patient without padding has several benefits including: simplified brace design and construction, less weight, lower profile, better ventilation, no absorption of water, easier cleaning, etc.

BRIEF DESCRIPTION OF THE DRAWINGS

FIGS. 8-11 illustrate enlarged detailed views of a portion of an embodiment of the brace;

FIGS. 39-40 illustrate dorsal and palmar views of a hand;

DETAILED DESCRIPTION

The present invention is directed towards a brace having a plurality of thin elongated beams that extend substantially in parallel along the length of the brace. The beams of the brace can be separated by a plurality of fenestrations that also extend substantially in parallel along the length of the brace. The adjacent beams are coupled together by posts that are substantially perpendicular to the beams. Each fenestration can be surrounded by two adjacent beams define the sides and two posts that define the ends of the fenestration. This configuration allows the brace to provide support for the limb and prevent bending but is also flexible and allows for radial expansion to provide a close fit with the limb.

Figure 1:
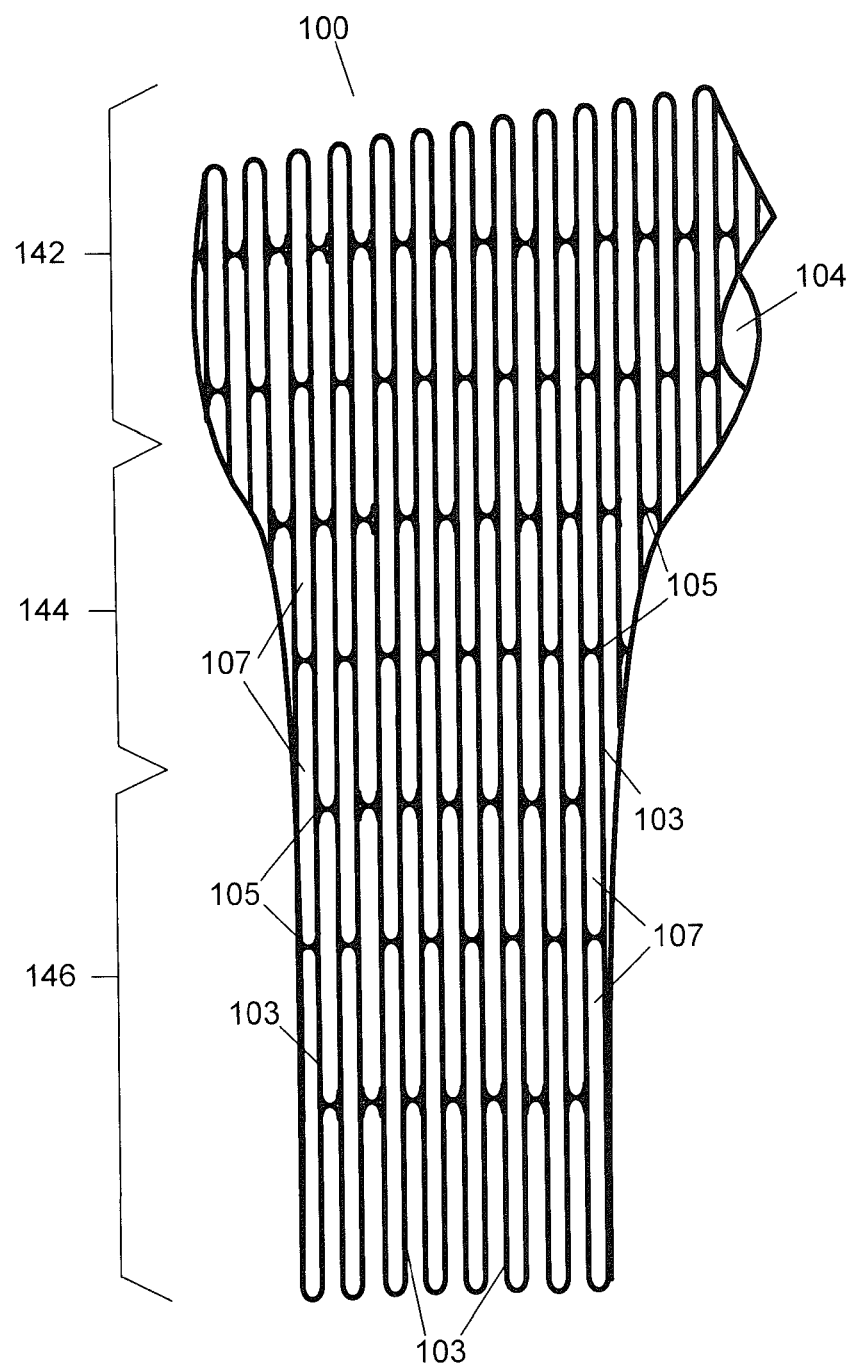
FIGS. 1-3 illustrate views of an embodiment of a brace with elongated fenestrations.
Figure 2:
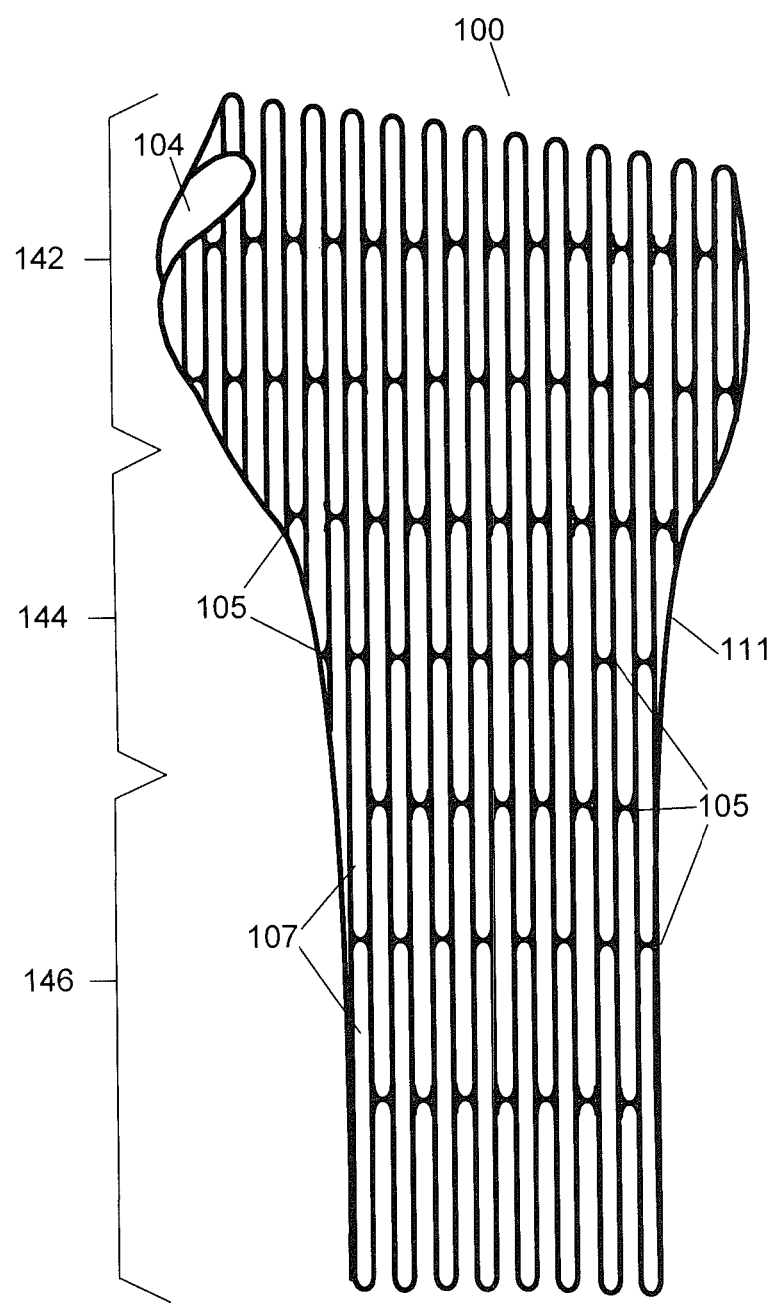
Figure 3:
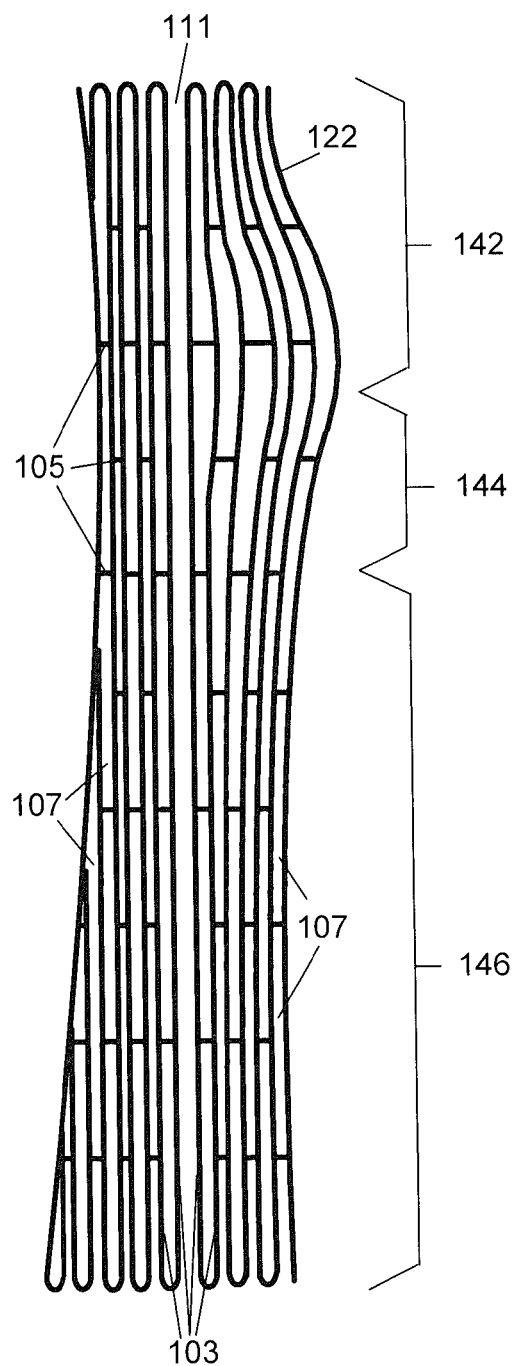

FIG. 1 illustrates a top dorsal view, FIG. 2 illustrates a bottom palmar view and FIG. 3 illustrates a side unular view of an embodiment of a brace 100. In the illustrated embodiment, the brace 100 can be an arm brace 100 that at least partially surrounds the patient's arm and can include a thumb hole 104. The brace can have a hand portion 142, a wrist portion 144 and a forearm portion 146. The brace 100 can be a generic design that may be available in a number of different sizes with each size fitting patients having limbs within a range of sizes. The brace 100 can be designed to resist specific types of arm movements. For example, the illustrated brace 100 may allow movement of the fingers and thumb as well as axial rotation of the hand so that the patient can grasp items, type on a keyboard and rotate door knobs to open doors. However, the brace 100 can also prevent the arm from bending of the wrist. This can be helpful in preventing injuries such as carpal tunnel syndrome. In this example, the brace 100 can be used to prevent movement of the patient's hand by holding the patient's wrist in a fixed predetermined position. Because the surface of the palm of the hand is normally concave, the inner surface of the brace 100 at the lower section of the hand portion 142 can include a convex surface 122 that corresponds to the concave surface of the palm.

The brace 100 can have a plurality of beams 103 that extend along the length of the brace 100. The adjacent beams 103 can be coupled by posts 105. A plurality of elongated fenestrations 107 also extend along the length of the brace 100. The sides of the fenestrations 107 can be defined by two adjacent beams 103 and the ends of the fenestrations 107 can be defined by two posts 105. The posts 105 can be arranged in a staggered manner so that all post 105 are separated by one or more fenestrations 107. In an embodiment, each post 107 can be coupled to one side of a beam 103 and the opposite side of the beam 103 can be adjacent to a mid section of a fenestration 107. Thus, the posts 105 are each separated from each other by at least one fenestration 107.

With reference to FIG. 3, an unular side view of the brace 100 is illustrated. In this embodiment, a seam 111 extends along the length of on the unular side of the brace 100. In other embodiments, the seam 111 can extend along any other portion of the brace 100. The seam 111 allows the brace 100 to be opened so that the limb can be placed in the brace 100.

Figure 4:
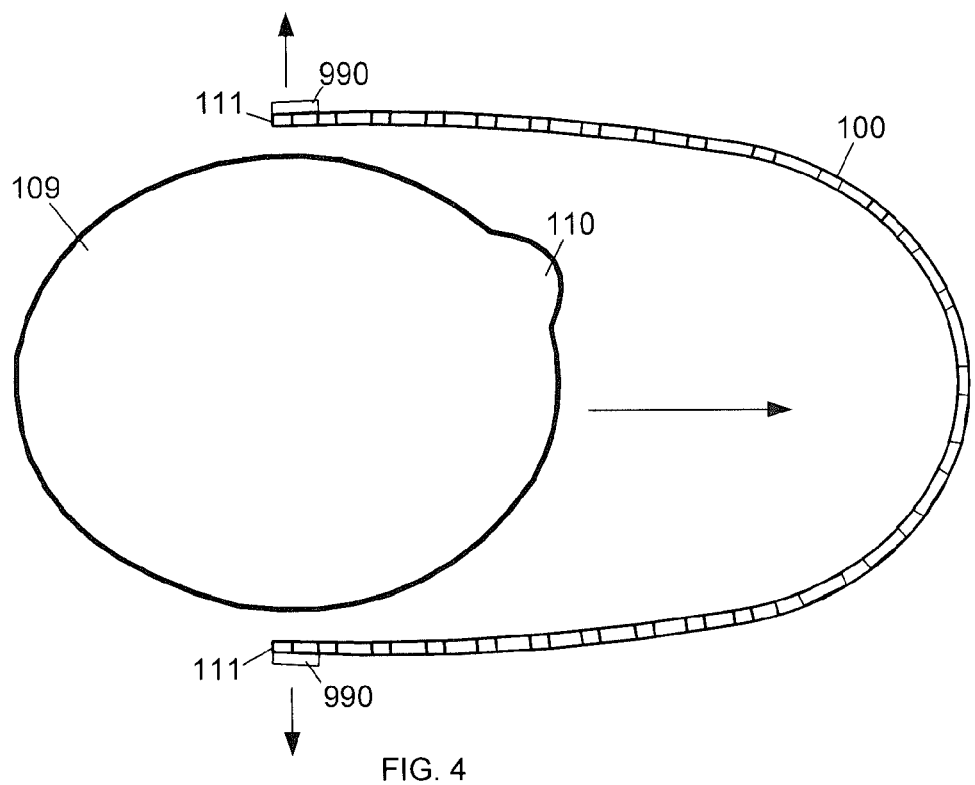
FIGS. 4-7 illustrate cross sectional views of an embodiment of the brace.
Figure 5:
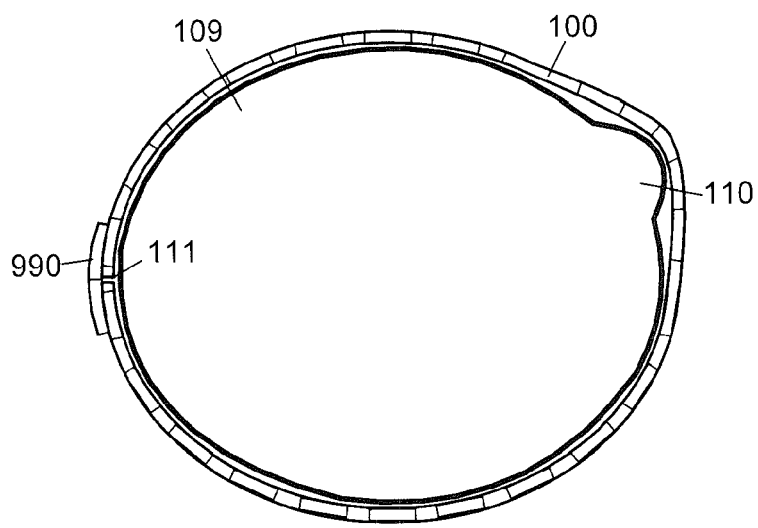
Figure 6:
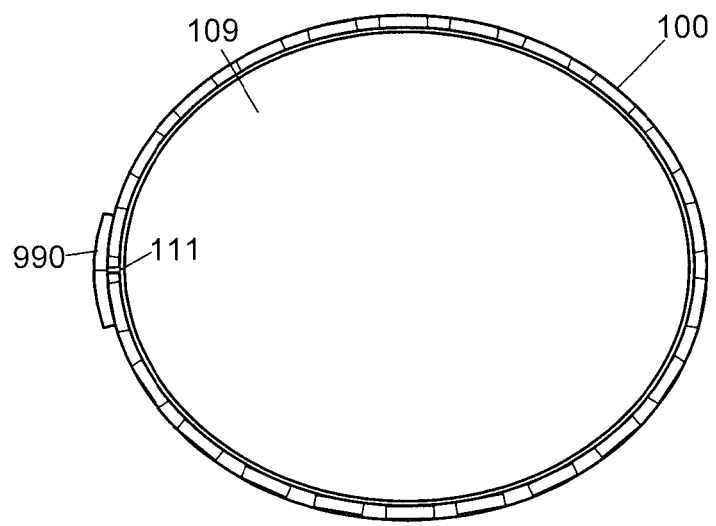

With reference to FIGS. 4-6, a proximal end view of an embodiment of the brace 100 is illustrated. With reference to FIG. 4, the seam 111 can be physically separated to open the brace 100 so that there is sufficient space to insert the limb 109 in the brace. The patient's thumb can be placed through the thumb hole 104 shown in FIGS. 1 and 2 and once the rest of the arm is placed in the brace 100 the seam 111 can be closed.

Figure 7:
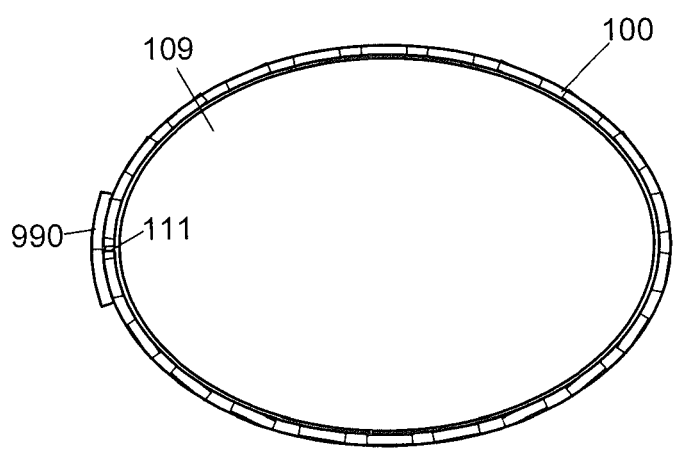

With reference to FIG. 5, once the limb 109 is placed in the brace 100, fasteners 900 can be used to couple the opposite sides of the brace 100 across the seam 111. The interior surfaces of the brace 100 can conform to the outer surface of the limb 109. If the limb 109 has a swollen area 110, the portion of the brace 100 over the swollen area 110 may expand radially to accommodate the shape of the swollen area 110. With reference to FIG. 6, as the limb 109 heals and the inflammation decreases, the swollen area 110 may no longer be present and the brace 100 can contract to conform to the changing dimensions of the outer surface of the limb 109. In many situations, the limb 109 may atrophy because it is held stationary and not being exercised. The brace 100 can continue to elastically adjust to the outer surface of the patient's limb as the cross section expands and contracts due to changes in temperature, atrophy, swelling, hydration or any other reasons. With reference to FIG. 7, the atrophy can cause the limb 109 to shrink in size and change in shape and the brace 100 can contract and conform to the change in the shape of the limb 109.

Figure 10:
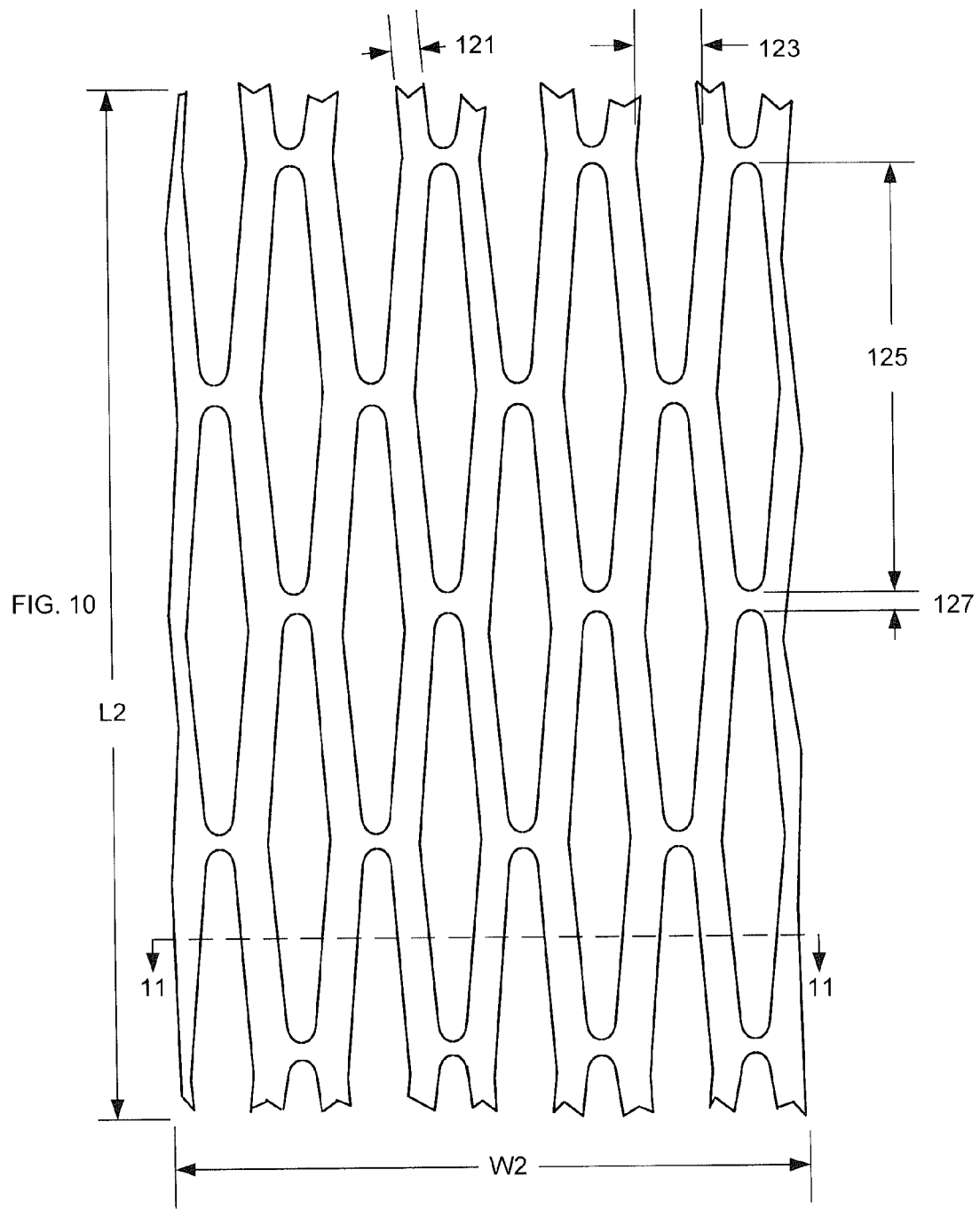
Figure 11:
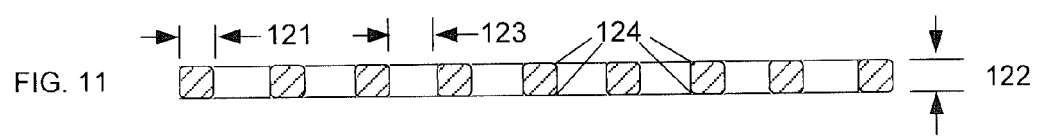

With reference to FIGS. 8-11, a portion of the brace 100 is illustrated showing a more detailed view of the beams 103, posts 105 and fenestrations 107. FIG. 8 illustrates a top view and FIG. 9 illustrates a cross sectional view of the portion of the brace 100 in the normal contracted state. The beams 103 are straight and the fenestrations are also straight in shape. The portion of the brace 100 can have a width W1 and a length L1. FIG. 10 illustrates a top view of the portion of the brace 100 in the expanded state and FIG. 11 illustrates a cross section of the portion of the brace 100 in the expanded state. As described above, the widths 121 of the beams 103 and the thickness 122 of the brace 100 can remain substantially the same. However, the widths 123 of the fenestrations 107 can expand in the expanded state. In the expanded state, the beams 103 can bend in a zigzag manner along the length and the sides of the fenestrations 107 are expanded to form elongated diamond shapes. The length of the beams 103 and fenestrations 107 can remain substantially the same, L1≅L2 and the width 123 of the fenestrations 107 and the width W2 of the portion of the brace 100 in the expanded state is larger, W2>W1. The dimensions of the beams 103, posts 105 and fenestrations 107 can vary over a range of dimensions and examples of possible dimensions are specified below in Table 1 with all dimensions in inches.

TABLE 1

| Beam Width | Post Width | Fenestration Length | Fenestration Width | Brace Thickness |
|---|---|---|---|---|
| 0.05-0.5 | 0.05-1.0+ | 0.1-5.0 | 0.05-1.0+ | 0.05-0.5 |

In the embodiment of the brace 100, the beams 103 illustrated in FIGS. 8 and 10 have rectangular cross sections. The exposed corners of the beams 103 and posts 105 can have a radius or a chamfer 124 to remove any sharp edges on the inner and/or outer surfaces of the brace 100. The radius or chamfer can range from about 0.01 to 0.2 inch. In other embodiments, the beams 103 and posts 105 can have any other type of cross sectional geometry such as: circular, oval, square, triangular, etc.

Figure 12:
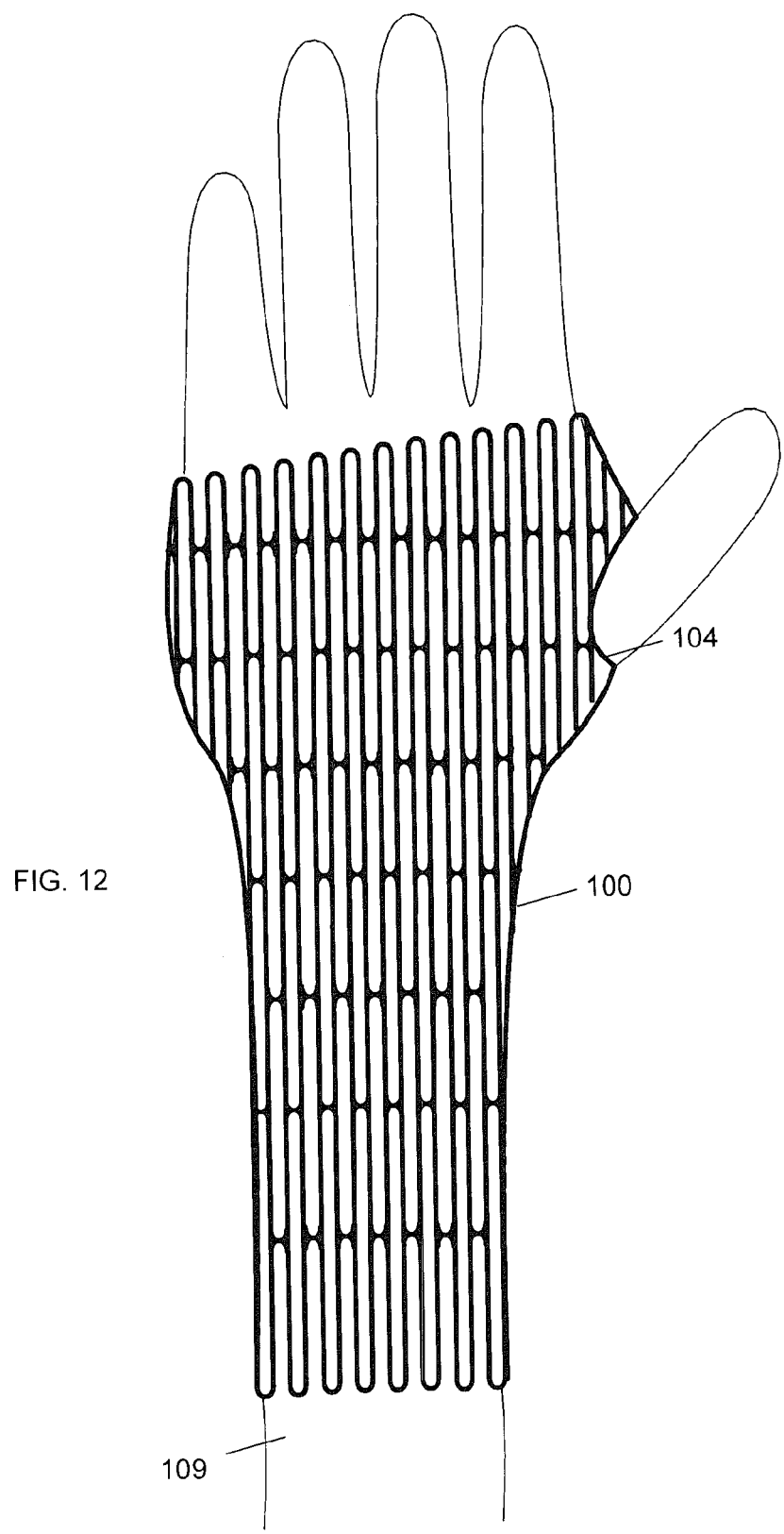
FIGS. 12-13 illustrate an embodiment of the brace on an arm of a patient.
Figure 13:
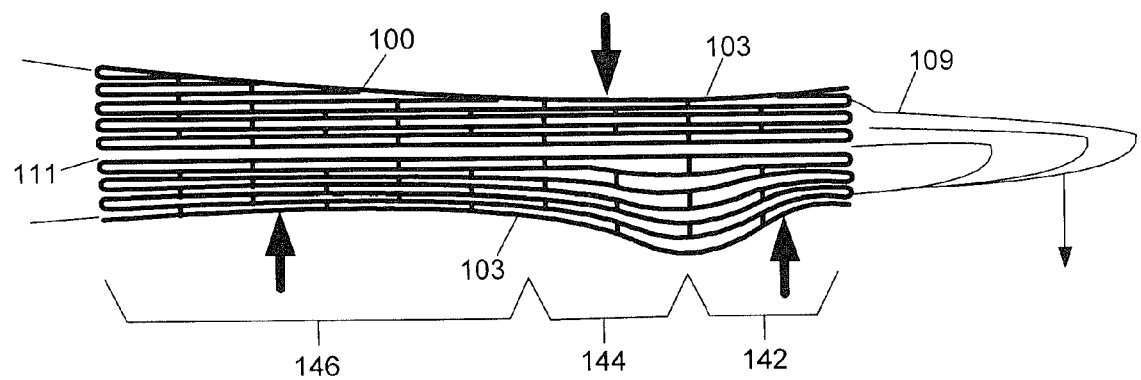

FIG. 12 illustrates top view and FIG. 13 illustrates a side view of an embodiment of the brace 100 on a patient's arm 109. The thumb is placed through the thumb hole 104 and the fingers extend through the distal end of the brace 100 and the forearm extends through the proximal end of the brace 100. With reference to FIG. 13, the brace 100 on the patient's arm 109 can resist bending forces applied to the brace 100. In this example, the patient may attempt to rotate the hand downward about the wrist. The brace 100 may counteract this movement by resisting the downward rotational force of the arm at the lower hand portion 142, the upper wrist portion 144 and the lower forearm portion 146. When the illustrated forces are applied to the brace 100, the beams on the upper portion of the brace 100 can be in tension and the beams 103 on the lower portion of the brace 100 can be in compression. The brace 100 will also similarly resist any movement of the arm 109 in any bending motion of the wrist. More specifically, the palm of the hand 135 will press against the lower section 117 of the distal portion 113 which will cause the middle section 115 to press down against the wrist 133 these forces will also rotate the brace 100 so that the proximal portion 111 presses up on the lower surface of the forearm 131.

The rigidity of the brace 100 will determine the amount of bending of the limb that is possible. If the brace 100 has a high axial rigidity the arm 109 will not bend about the wrist. However, if the brace 100 can be made of an elastic material, some bending of the arm 109 may be possible. By know the mechanical properties of the material being used and the brace design dimensions, the bending characteristics can be designed into the brace 100. Thus, the brace 100 can be fabricated so that the axial rigidity is within a specific range based upon the needs of the patient. For example, a brace made for an adult may need to be more rigid than a brace made for a small child in order to provide the required limb movement resistance and/or support. The illustrated bending forces can result in the beams 103 on the upper side of the brace 100 being in tension and the beams 103 on the lower side being in compression. The bending properties of the beams 103 can control the bending rigidity of the brace 100.

Figure 14:
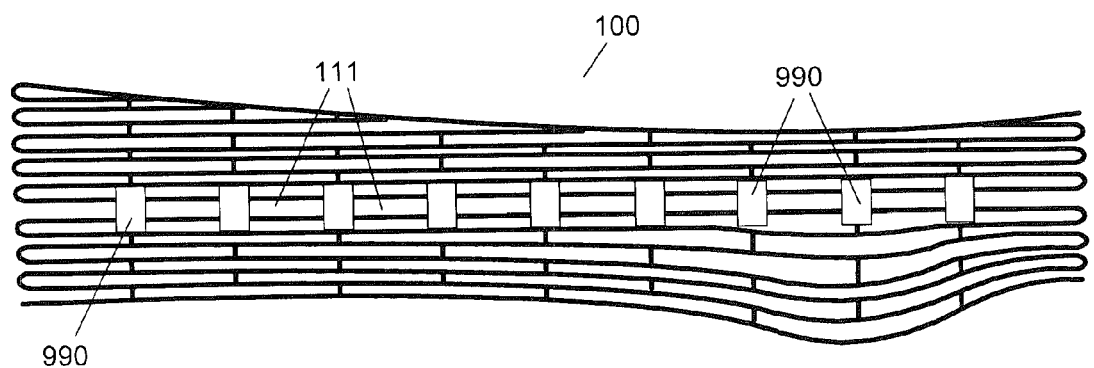
FIG. 14 illustrates a side view of an embodiment of a brace with fasteners.
Figure 15:
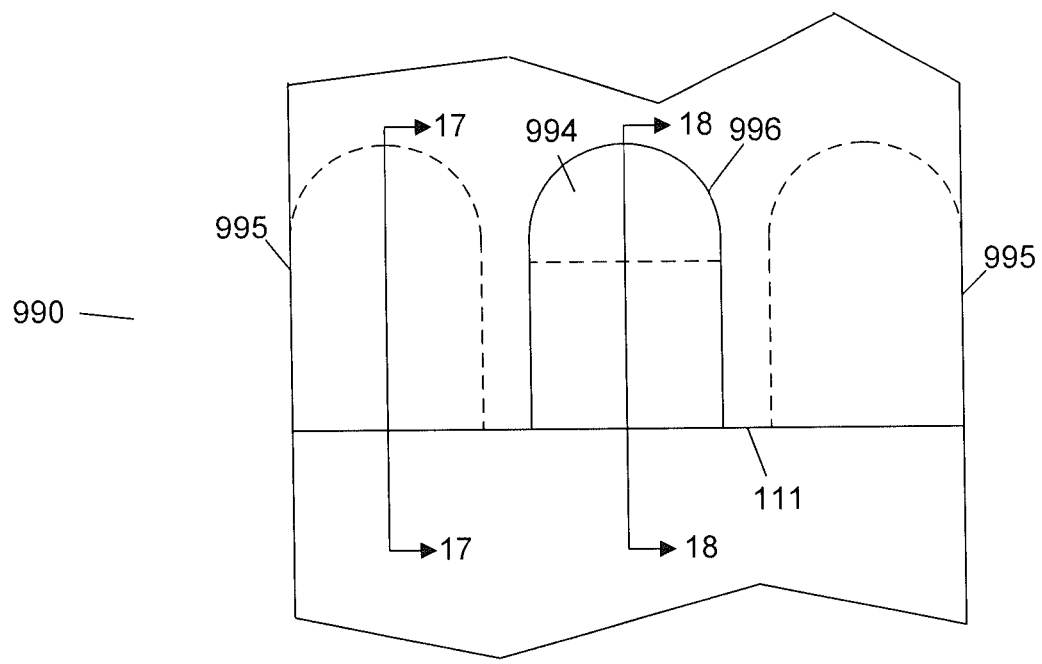
FIGS. 15-28 illustrate an embodiment of a fastener.
Figure 16:
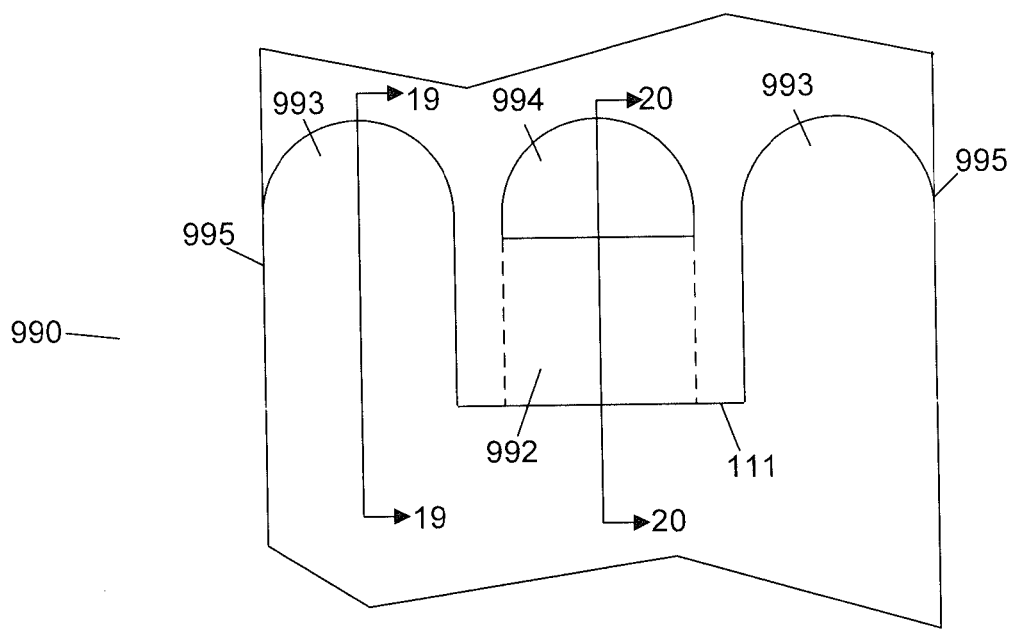

FIG. 14 illustrates an embodiment of the brace 100 with a plurality of fasteners 990 that extend across the seam 111 of the brace 100 and FIGS. 15-28 illustrate an embodiment of a fastener 990 that can be used to secure the opposite sides of the brace 100. With reference to FIGS. 15 and 16, a top view and a bottom view of an adjustable fastener 990 that can be used to connect opposite sides of a seam 111. In this example, the seam 111 is illustrated as being a straight line. In other embodiments, a different number of the fasteners 990 can be used and placed at different positions and the seam 111 can be curved.

Figure 17:
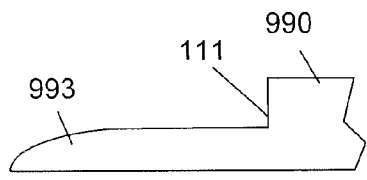
Figure 18:
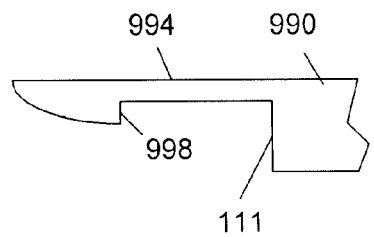

With reference to FIGS. 17 and 18, in an embodiment, the adjustable fastener 990 can include a plurality of tabs 993, 994 that extend from the second section 992 and grooves 995, 996 that are formed in the first section of the fastener 990. Details of an embodiment of the tabs 993 and 994 are illustrated in FIGS. 17 and 18 respectively. FIG. 17 illustrates a cross section side view of tab 993. The front end of the tab 993 is tapered and the bottom surface can be the interior or exterior surface of the brace. FIG. 18 illustrates a cross section view of tab 994 which has a front end that is tapered and a latch 998 that locks the adjustable fastener 990 together. The top surface of the tab 994 can be the interior or exterior surface of the brace 100.

Figure 19:
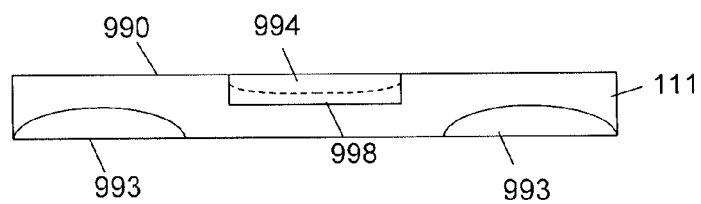
Figure 20:
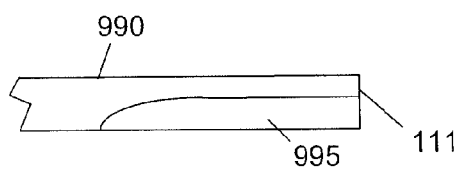
Figure 21:
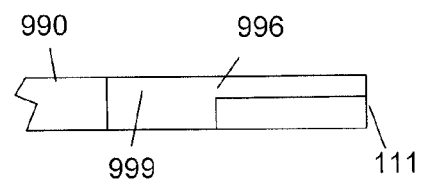
Figure 22:
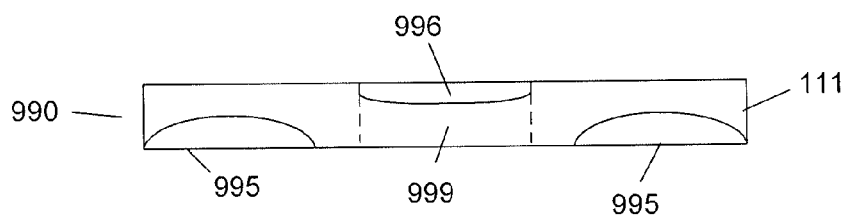

With reference to FIG. 19, a front view of the tabs 993 and 994 is illustrated. The tab 998 can be a locking protrusion that engages one or a plurality of recesses 980 formed across the groove 996. Details of the grooves 995 and 996 are illustrated with reference to FIGS. 20 and 21 respectively. FIG. 20 illustrates a cross section side view of the groove 995. The groove 995 in the first section 991 includes a concave surface formed in the lower surface of the first section 991 that extends inward from the seam 111. FIG. 21 illustrates an embodiment of a cross section side view of the groove 996. The groove 996 can be formed in the upper surface of a section of the fastener 990 and extend inward from the seam 111. The groove 996 can include a plurality of recesses 980 that extend across the groove 996 and the groove 996 may be connected to a through hole section 999 that extends between the upper and lower surfaces of a section of the brace 100. FIG. 21 is a front view of the grooves 995, 996.

Figure 23:
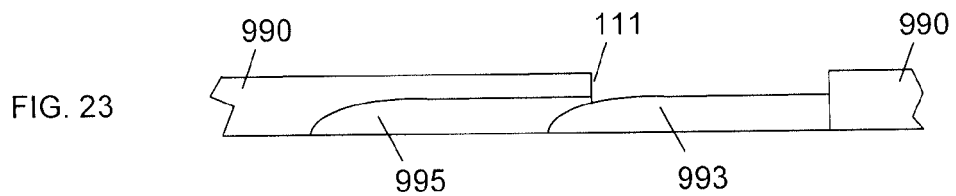
Figure 24:
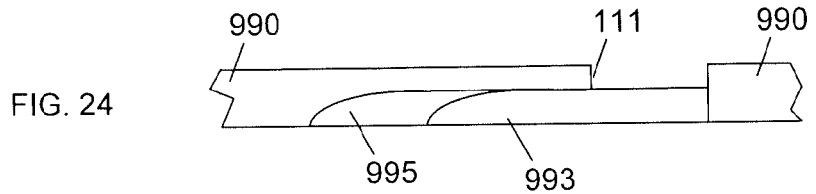
Figure 25:
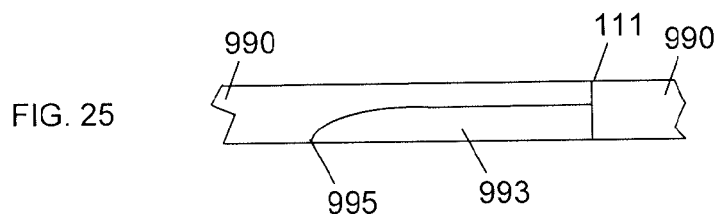
Figure 26:
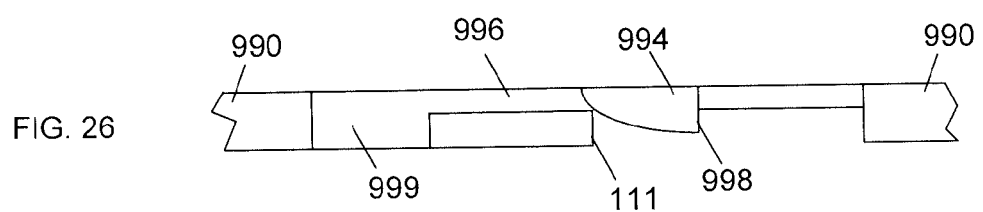
Figure 27:
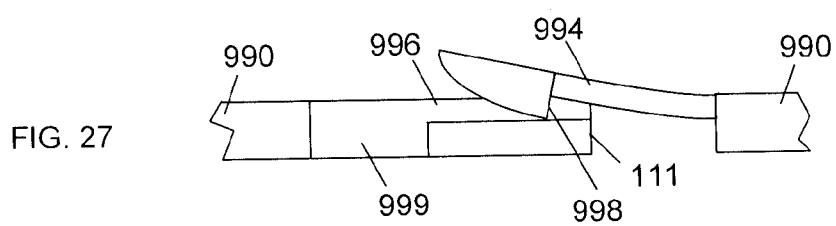
Figure 28:
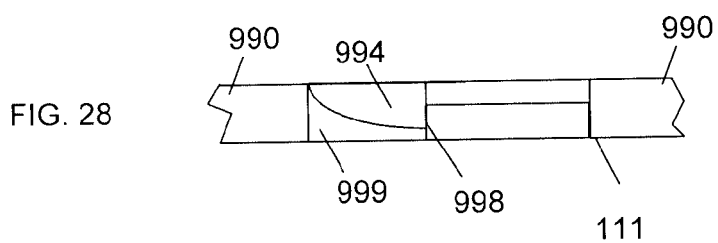

With reference to FIGS. 23-28, cross section side views of the tabs 994, 995 being inserted into the grooves 995, 996 to connect the first section and the second section of the fastener 990 are illustrated. FIG. 23 illustrates the tab 993 entering the groove 995. FIG. 24 shows the tab 993 partially in the groove 995 and FIG. 25 shows the tab 993 fully inserted into the groove 995. The bottom of the tab 993 can remain flush with the bottom of the first section of the fastener 990. When fully inserted, the first section of the fastener 990 is coupled to the second section of the fastener 990 along the seam 111. FIG. 26 shows the tab 994 entering the groove 996. FIG. 27 shows the tab 994 partially in the groove 996 and deflected upward. FIG. 28 shows the tab 994 fully inserted into the groove 996 with the protrusion 998 within one of the recesses 980 to lock the tab in place. In this embodiment, the first section and the second section of the fastener 990 can only be separated by deflecting the tab 994 to remove the protrusion 998 from the recesses 980. The connector illustrated in FIGS. 23-28 can be an integrated curved design that conforms to any curved surface of the brace 100 and can provide a rigid connection across the seam 111.

Figure 29:
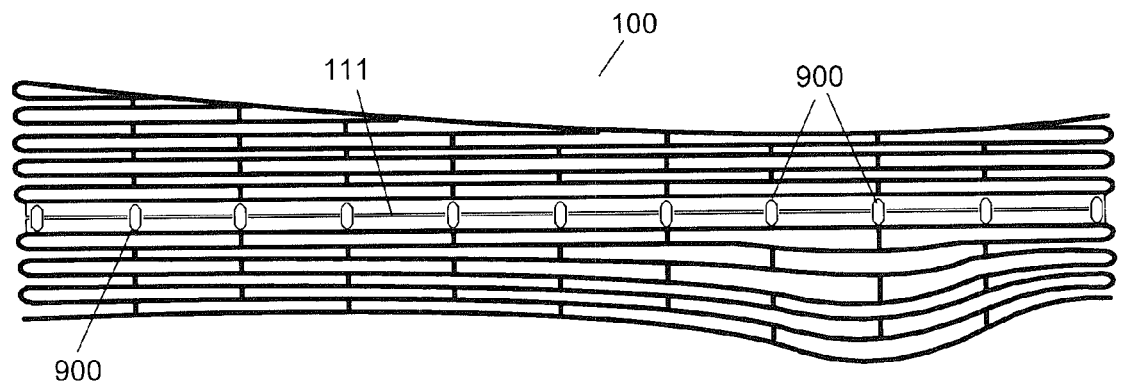
FIG. 29 illustrates a side view of an embodiment of a brace with fasteners.

FIG. 29 illustrates a side view of a brace 100 with another connection mechanism 900 that extend across the seam 111 of the brace 100. In other embodiments, a different number of the fasteners 900 can be used and placed at different positions and the seam 111 can be curved. In an embodiment, the coupling member 471 can be created as an integrated portion of the brace 100. For example, if the brace 100 is fabricated using a 3D printing machine, the connection mechanisms 900 can be formed with the brace 100 as a single integrated structure. However, in other embodiments, the connection mechanism 900 can include a separate component that is attached to the brace 100 but may not be an integrated part of the brace 100 that is formed simultaneously.

Figure 30:
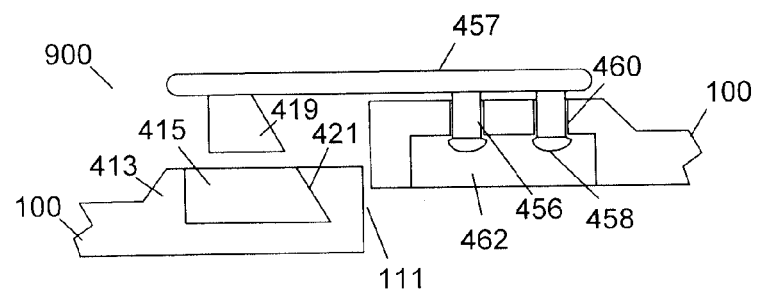
FIGS. 30-34 illustrate detailed views of different fastener embodiments.
Figure 31:
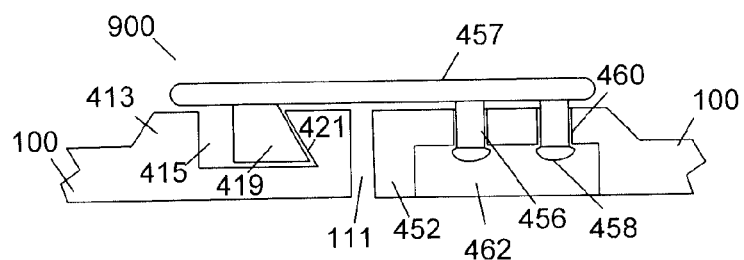

FIGS. 30 and 31 illustrate cross section side views of a portion of an embodiment of the connection mechanism 900. The coupling member 471 can be a separate structure that includes one or more fastening pins 456 that have flared tips 458 and are placed through holes 460 in the brace 100. The diameter of the pins 456 can be smaller than the diameter of the holes 460 but the outer diameter of the tips 458 can be larger than the diameter of the holes 460. By pressing the flared tips 458 through the holes 460, the coupling member 471 is secured to the brace 100. The brace 100 can have a recessed portion 462 so that the tips 458 are above the inner surface of the brace 100. This design also allows the adjustable member to be replaced if necessary. For example, the coupling member 471 may break or a different length adjustable member can be used to provide a better fit on the patient. In an embodiment, the adjustable member can be stocked in various lengths and attached to the brace 100 after it has been fabricated.

Figure 32:
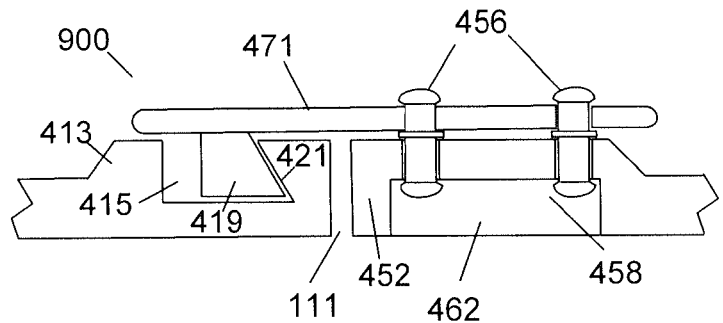

To secure the brace 100 around the forearm, a hook 419 at the end of the coupling member 471 can be manually placed over the corresponding hole 415 as shown in FIG. 30. The hook 419 is then placed into the hole 415 as shown in FIG. 31. The tension on the coupling member 471 will cause the hook 419 to engage the corresponding angled surface 421 within the hole 415 and hold the coupling member 471 to the hole 415. The patient can also release the hook 419 from the hole 415 by pulling the end of the coupling member 471 out of the hole 415 to release the adjustable member 457. With reference to FIG. 32 another embodiment of a coupling member 471 is illustrated with two pins 456 that extend through holes in the coupling member 471.

Figure 33:
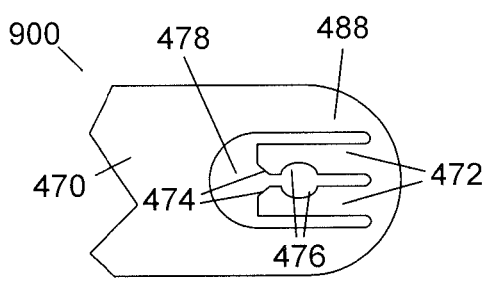
Figure 34:
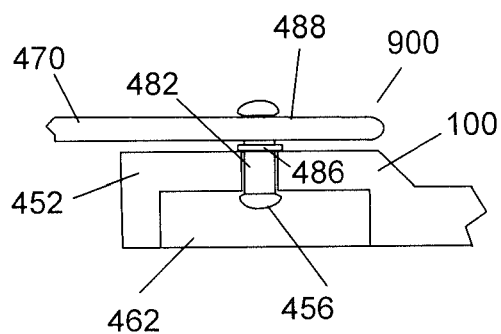

FIGS. 33 and 34 illustrate more detailed views of another embodiment of an end of a connection mechanism 900 that extend across the seam 111 to close the brace 100. FIG. 33 illustrates a top view and FIG. 34 illustrates a cross section side view of the connection mechanism 900. In this embodiment, the connection mechanism 900 can include a coupling member 470 having a clip mechanism 488 at one end and a hook 419 at the opposite end. The clip mechanism 488 can include two elongated prongs 472 that have tapered ends 474 and clip holding sections 476. The ends of the prongs 472 can be coupled to the coupling member 470 and may be flexible to allow for some elastic deflection. The clip mechanism 488 can also have an open space 478 adjacent to the tapered ends 474. The clip mechanism 488 can be clamped around a pin 482 having flared tips 458 at the ends and a center flange 490. The pin 482 can be inserted into a hole in the brace 100 having an inner diameter that is smaller than the outer diameter of the flared tip 458 and the lower flared tip 458 can extend into a recessed portion 462. The flange 486 can rest against the outer surface of the brace 100 to keep the upper portion of the pin 482 extending away from the brace 100. The upper portion of the pin 482 can be placed into the open space 478 and clip mechanism 488 can be moved around the pin 482 so the prongs 472 spread apart and slide under the upper flared tip 458 until the upper portion of the pin 482 is positioned within the clip holding sections 476 of the prongs 472. The clip holding sections 476 of the prongs 472 will hold the clip mechanism 488 in place on the pin 482.

Figure 35:
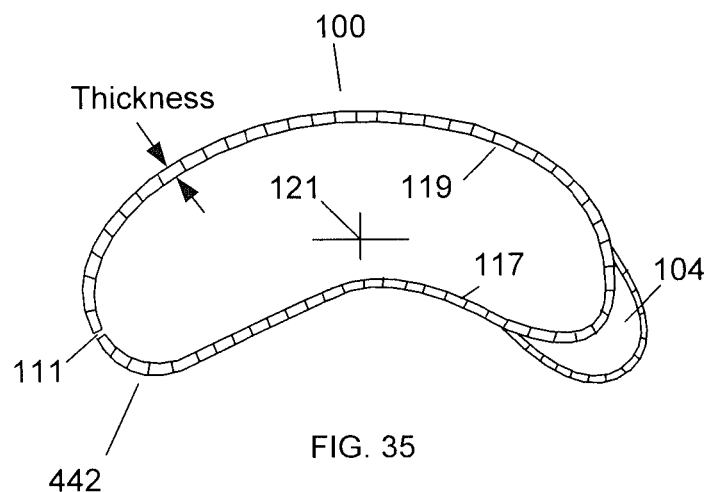
FIG. 35 illustrates a distal end of an embodiment of the brace.
Figure 36:
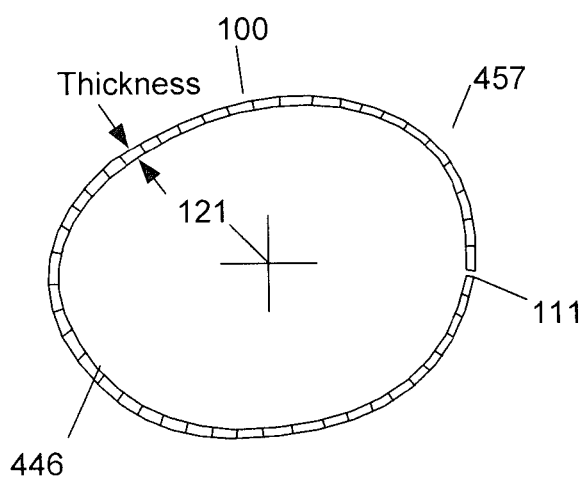
FIG. 36 illustrates a proximal end of an embodiment of the brace.

FIG. 35 illustrates a front view of the brace 100 at the distal hand section 442 and FIG. 36 illustrates an end view of the brace at the proximal end 446. The brace 100 has an inner surface that corresponds to an arm and defines a center axis 121. The brace 100 can allow the hand to rotate about the center axis 121. Because the upper section 119 and the lower section 117 of the distal end fit closely around the hand, the distal portion 442 can remain stationary on the hand, but the middle portion and the proximal end 446 can rotate around the forearm of the patient if the wrist is rotated about the center axis 121.

Figure 37:
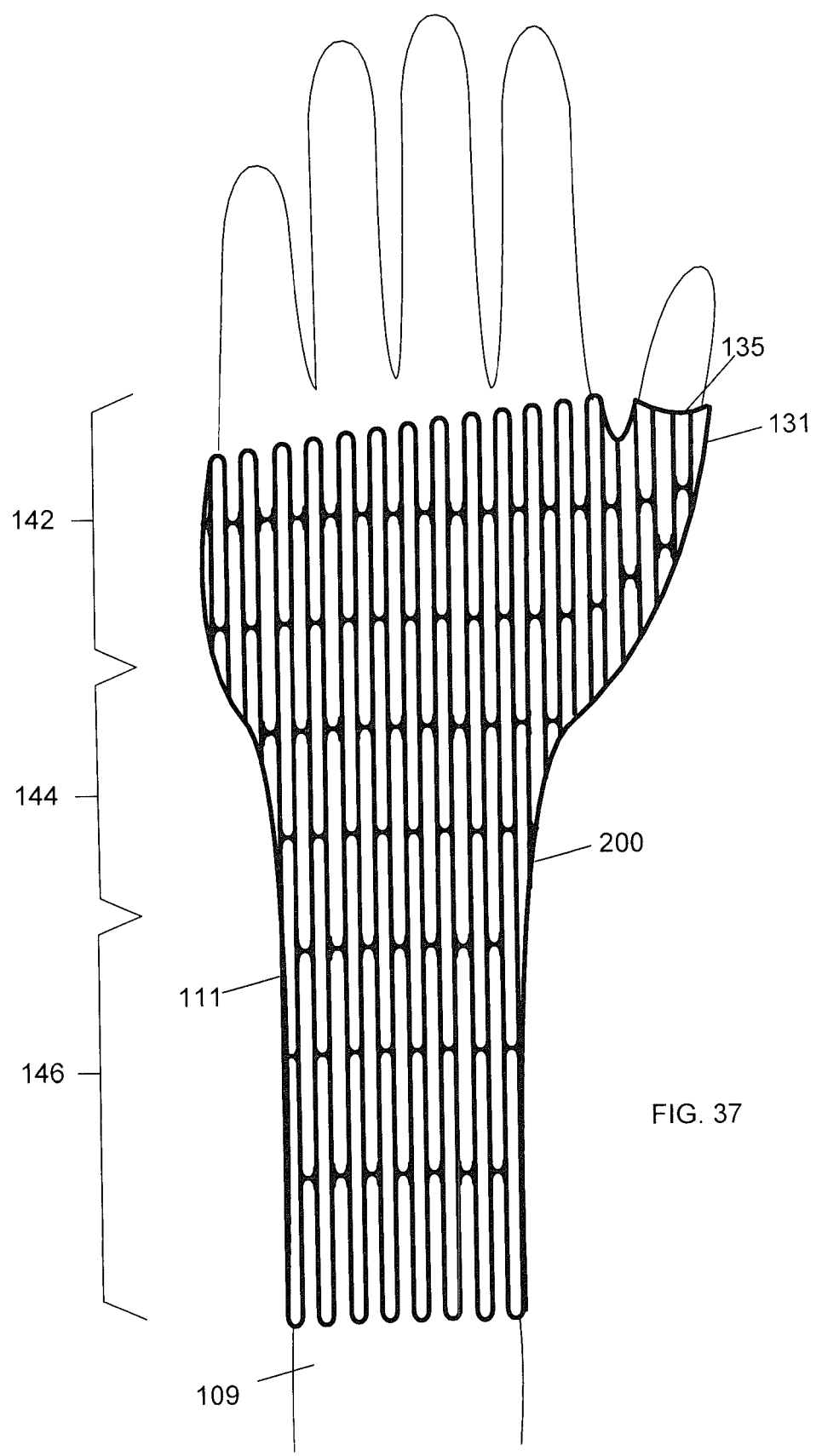
FIG. 37 illustrates a view of a brace with a thumb support on an arm.

With reference to FIG. 37, a top dorsal view of an embodiment of a brace 200 that restricts the movement of the thumb is illustrated. In this embodiment, the brace 200 includes a thumb section 131 that extends up a portion of the thumb. Since the thumb is surrounded by the thumb section 131, the brace 200 restricts the movement of the thumb relative to the hand. In this embodiment, the thenar section 115 may also cover the thenar crease to further restrict movement of the thumb. In order to place the brace 200 onto the arm 109, the hand may first be placed into the distal portion 142 with the thumb placed through the thumb hole 135. The wrist section 144 and the proximal section 146 can then be positioned around the arm 109 and the fasteners can then be coupled across the seam 111 to secure the brace 200 to the arm 109. Although the seam 111 is illustrated on the ulnar side of the brace, in other embodiments, the seam 111 can be along any other portion of the brace 100.

Figure 38:
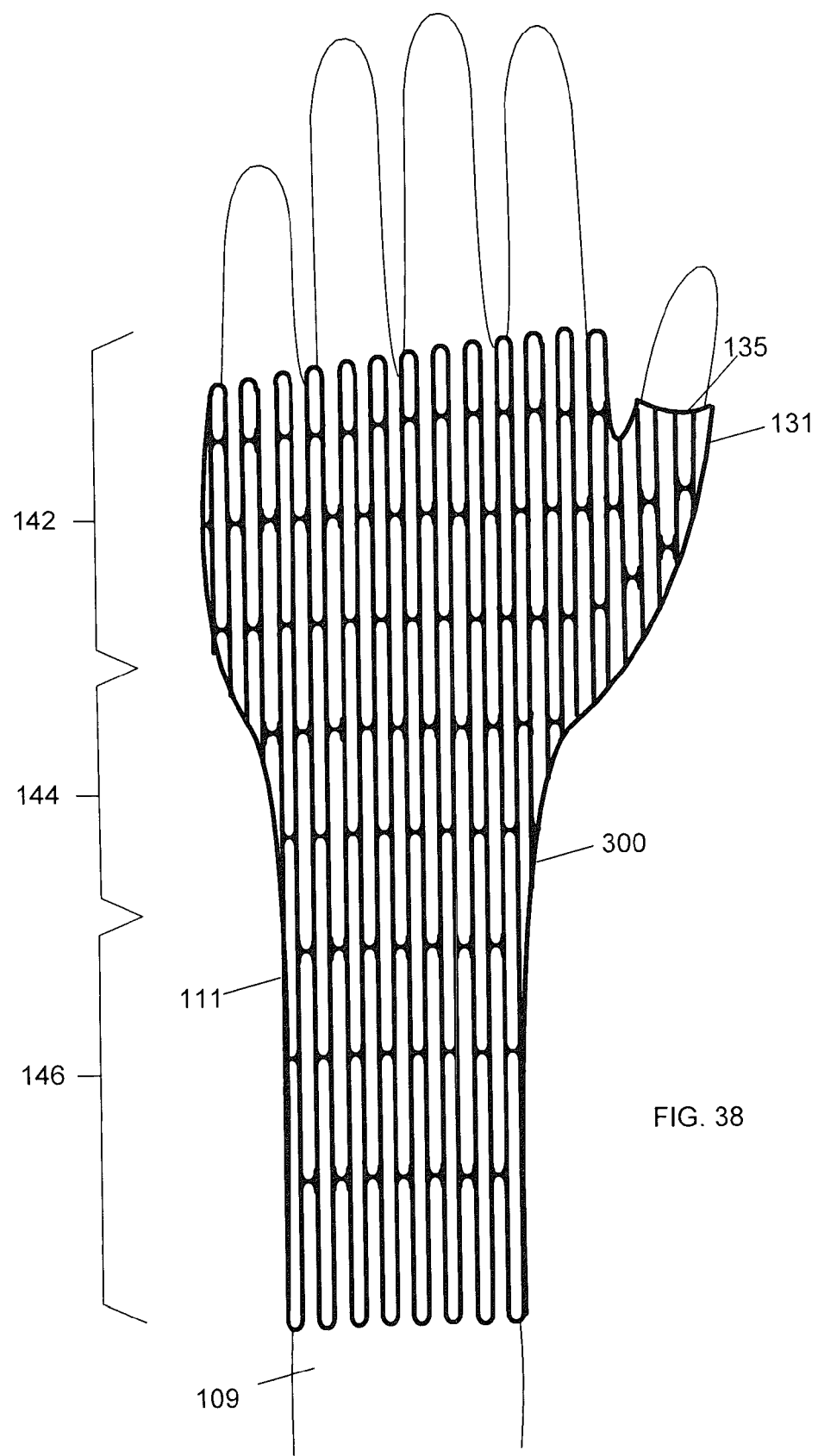
FIG. 38 illustrates a view of a brace with finger and thumb supports on an arm.
Figure 41:
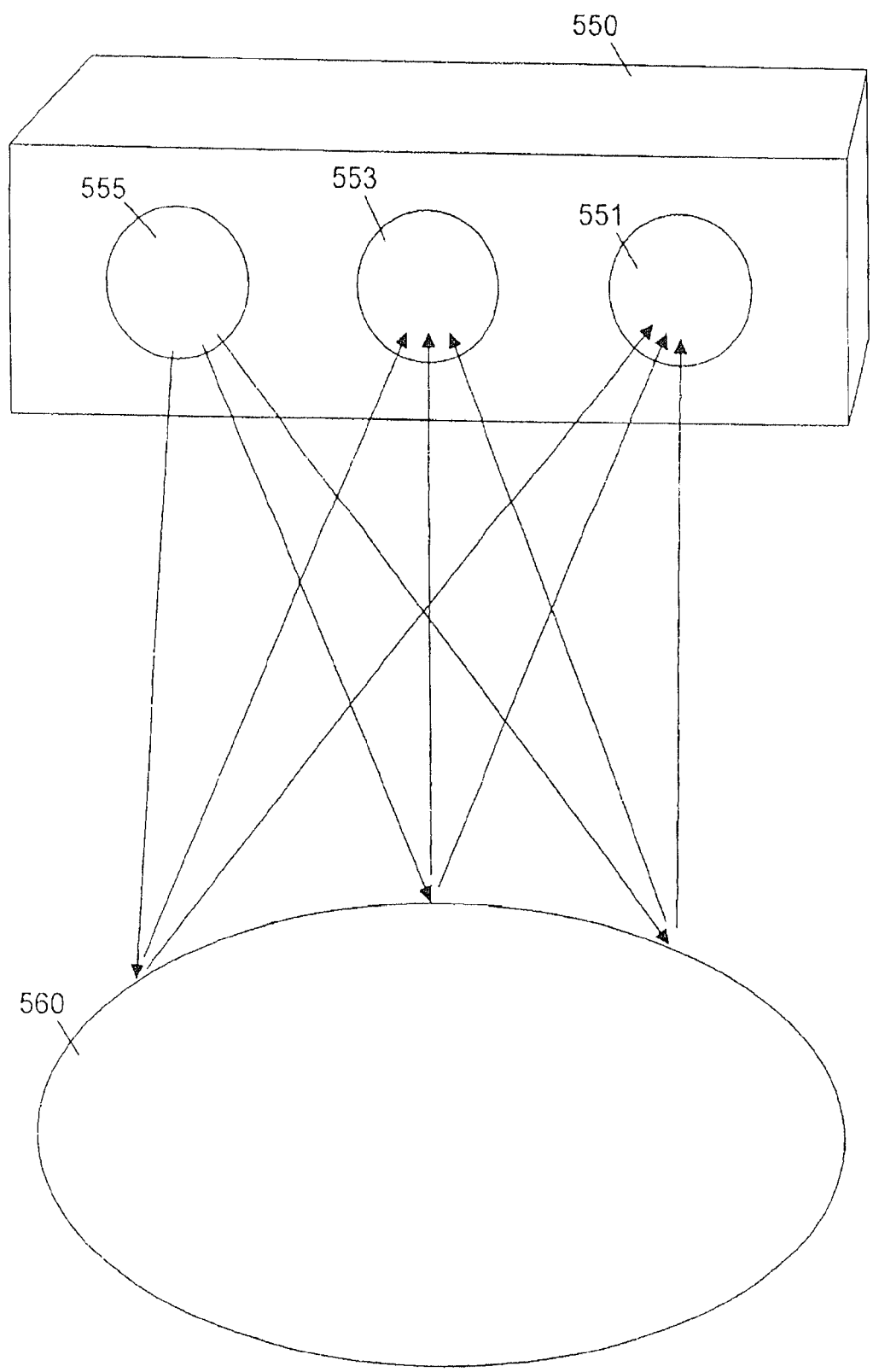
FIGS. 41-44 illustrate IR and visible light photographic systems for detecting a surface of a patient.

With reference to FIG. 38, an embodiment of a brace 300 is illustrated that prevents movement of the hand and the lower thumb and restricts the movement of the fingers. In this embodiment, the distal portion 142 may extend around the bottom portion of the fingers and the brace 300 may also include a separate thumb section 131 and a thumb hole 135. The distal portion 142 may cover the proximal phalanx segments 221 of the fingers and extend over the knuckles of the hand. The thenar crease may also be covered by the distal portion 142. Thus, the hand movement may be more restricted by the brace 300 than the other illustrated braces 100 and 200. In order to place the brace 300 onto the arm, the hand may first be placed into the distal portion 142 with the thumb placed through the thumb hole 135 and the middle section 144 and the proximal section 146 can then be placed around the arm 109. The fasteners can then be coupled across the seam 111 to secure the brace 200 to the ulnar side of the brace 100, in other embodiments the seam 111 can be located on any other side of the brace 100. In other embodiments, braces can be designed to allow or prevent any other limb movements.

With reference to FIGS. 39 and 40, a hand and specific anatomical structures are illustrated. FIG. 39 illustrates a palmar side of the hand and FIG. 40 illustrates a dorsal side of the hand 135. The anatomical structures include: the proximal phalanx segments 221 of the fingers, the palmar digital creases 231, the distal palmar crease 223, the proximal palmar crease 225, the thenar crease 227 and the wrist crease 229. Because the fingers bend towards the palmar side of the hand 135, these creases may only be visible on the palmar side of the hand 135. The hand 135 may also include anatomical points that can be marked with stickers or any other type of markings that can improve the accuracy of the measurements for these points. These marked anatomical points can include: finger knuckles 224, the thumb knuckle 226, radial styloid 228, and the ulnar styloid 230. The knuckle and styloid points may be marked on either side of the hand. In an embodiment, the knuckle and styloid points can be marked on one side of the hand 135 and the system can identify these points and points for these anatomical features on the opposite side of the hand. For example, if the knuckle and styloid points are identified on the surface of the dorsal side, the system can process this information and also identify the locations of the knuckle and styloid points on the surface of the opposite palmar side of the hand 135. The system can also function in the reverse manner with the system identifying points marked on the dorsal side of the hand based upon markings on the palmar side of the hand In an embodiment, the system can use the location information to design a portion or the entire the brace. The system can design the brace either with additional input from a brace designer or fully automatically.

By identifying and referencing these visible anatomical features of the hand during the design process, the spiral brace can be designed to cover specific areas of the hand to prevent specific types of movement or avoid certain areas of the hand to allow movement of specific joints or parts of the hand or limb. In an embodiment, the photographic process used to create a digital representation of the body may be able to identify these features and provide graphical identifications of these features on a display coupled to a design computer. The brace can then be designed to restrict or accommodate movement of specific areas of the hand. In an embodiment, measurements of the anatomical features can be made of many different people and the geometry of the brace 100 can be based upon average values for these measurements. Different sizes of the brace 100 can be made to provide a proper fit for as many limb sizes and shapes as possible. If a limb does not properly fit one of the stock braces, a custom brace 100 may be produced based upon the limb measurements.

The braces can be designed to have a smooth inner surfaces that corresponds closely to an average or normal patient's body for stock off the shelf products or a custom inner surface for a specific patient. The cast or brace can be designed by an industrial designer using a Computer Aided Design (CAD) computer program. The mechanical data for a patient can be obtained from visible or infrared (IR) light photographs of the patient's body or limb. This body topography can be determined from the photographs and the topography data is then digitized and input into a CAD program that is referenced to design the cast or brace. An example of a suitable CAD program is Pro/Engineer by Parametric Technology Corporation. Other CAD software includes: SotidWorks by SolidWorks Corporation a subsidiary of Dassault Systemes, S. A. For simplicity, the inventive custom brace, cast or device will be described as a leg brace, however the same processes can be used to form an arm or back brace or any other body brace, cast or device. The brace can be a hard and strong structure that is designed to surround and support the injured portion of the body or limb.

In an embodiment, the braces disclosed by the application are designed as a single integrated structure. Although, the braces are shown for hands and forearms, in other embodiments, the inventive braces may also be designed and used for any other portion of the patient's body including elbows, feet, legs, ankles, knees, back, neck, shoulders, and other portions of the body. For example, a leg brace is created for a patient using a CAD system. The leg brace can include an upper leg, knee, lower leg, and foot and have an interior surface that matches the mechanical dimensions and surface contours of the patient's leg. In order to accurately create an interior surface that matches the patient's leg, the surface counters of the user's leg are measured. The measurement of the outer surface of the leg can be obtained in several different ways. In a preferred embodiment, a photogrammetry, depth mapping or image correlation technique or other type of photographic surface detection method is used to obtain the outer surface measurements which can be a set of 3-dimensional coordinates that define the outer surface of the patient's leg or any other body part.

Photogrammetry in its broadest sense reverses the photographic process by converting flat 2-dimensional images of objects back into the real 3-dimensional object surface. Two or more different photographs can be required to reconstruct a 3-dimensional object. In a perfect photogrammetry process, two photographs would provide enough information to perfectly reconstruct the 3-dimensional object. Unfortunately, the photography and measuring process are generally not perfect so the reconstruction of the 3-dimensional object based upon two photos will also have defects. The photogrammetry object measurement process can be improved by taking more photographs and using the extra information to improve the accuracy. The photogrammetry process will produce a set of 3-dimensional coordinates representing a surface of an object from the measurements obtained from the multiple photographs.

Photogrammetry uses the principle of triangulation, whereby intersecting lines in space are used to compute the location of a point in all three, XYZ dimensions. In an embodiment, multiple cameras are used to photograph the leg or body part simultaneously. In other embodiments, a light from a light source that is a known distance from a camera is projected onto a patient and a photograph of the patient is taken. By triangulating each of the points of light, the distances from the camera to each point of light can be determined. In order to triangulate a set of points one must also know the camera positions and aiming angles also called the "orientation" for all the pictures in the set. A process called resection is used to determine the camera positions and aiming angle calculations for each camera. The cameras should also be calibrated so their errors can be defined and removed.

Triangulation is the principle used by photogrammetry to produce 3-dimensional point measurements. By mathematically intersecting converging lines in space, the precise locations of the points can be determined. Photogrammetry can simultaneously measure multiple points with virtually no limit on the number of simultaneously triangulated points. By taking pictures from at least two or more different locations and measuring the same target in each picture a "line of sight" is developed from each camera location to the target. Since the camera locations and aiming directions are known, the lines can be mathematically intersected to produce the XYZ coordinates of each targeted point. When a pattern of IR or visible light points are projected onto the patient, triangulation can also be used to determine the locations of these points based upon the distance between the light source and the camera and the detected angles of the points.

Resection is the procedure used to determine the coordinates of the object from photograph data, based upon the camera positions and aiming directions, also known as the orientation of the camera. Typically, all the points that are seen and known in XYZ coordinates in the image are used to determine this orientation. For an accurate resection, you may have at twelve or more well-distributed points in each photograph. If the XYZ coordinates of the points on the object are known, the camera's orientation can be computed. It is important to realize that both the position and aiming direction of the camera are needed for resection. It is not sufficient to know only the camera's position since the camera could be located in the same place but be aimed in any direction. Consequently, the camera's position which is defined by three coordinates, and where it is aimed which is defined by three angular coordinates must be known. Thus, although three values are needed to define the X, Y and Z coordinates of a target point, six values may be required to define a point on a picture, XYZ coordinates for position, and XYZ angles for the aiming direction.

The surface being photographed should also have a minimum number of well-distributed reference points that appear on each photograph and for an accurate surface measurement. The reference points can be visible marks placed on the object that provide a visible contrast that will be clearly shown on the photographs. There should be at least twelve well-distributed reference points on each photograph and at least twenty points for the entire surface of the object. The reference points should be evenly distributed on the object and throughout the photograph. The surface of the object can be more accurately measured with a larger number of reference points.

In an embodiment, the patient's natural features including: freckles, spots, wrinkles, pores and other features can be used as the reference points. Alternatively, IR or visible light can be projected onto the patient to provide the reference points for photographic measurement. It is also possible to mark the patient's skin with ink markers and in an embodiment, the patient or patient's limb can be covered with a form fitting material such as an elastic cotton tube, stockinette, leotard, body suit. This process can be repeated for many people if generic braces in multiple sizes are being designed.

In an embodiment, a computer program processes the photographic measurements to produce the final XYZ coordinates of all the measured points. In order to do this, the program triangulates the target points and resects the pictures. The program may also calibrate the camera. Typical accuracies of the three dimensional measurements can be very high under ideal operating conditions. For example, the measurements can be accurate to 50-100 microns (0.002" to 0.004"). However, the accuracy of a photogrammetric measurement can vary significantly since accuracy depends on several inter-related factors. Important accuracy factors include: the resolution and quality of the camera, the size of the object being measured, the number of photographs taken, and the geometric layout of the pictures relative to the object and to each other.

Photogrammetric measurements can be dimensionless. To scale a photogrammetric measurement, at least one known distance is required. The known distance can be a distance marked on the object, a known distance between cameras or a known distance between a light source and a camera. For example, if the actual coordinates for some targeted points are known, the distances between these points can be determined and the points can be used to scale the measurement. Another possibility is to use a fixture with targets on it and measure the fixture along with the object. Because the distance between the targets on the fixture is known, it can be used to scale the other measurements between reference points on the object. Such fixtures are commonly called scale bars. The patient topography dimensions can also be determined by knowing a distance between two cameras and the angles of lines between the cameras and the points on the patient. From this information, the distances between the cameras and the points on the patient can be determined by triangulation. Similarly, the patient topography dimensions can also be determined by knowing a distance between a light beam source and a camera, an angle of the light beams from a source and the angles of the light points detected by the camera. From this information, the distances between the camera and the light points on the patient can be determined by triangulation. The light can be infrared and the camera can be an infrared camera that produces infrared photographs.

In an embodiment, the inventive method is used to make a cast or a brace for an injured limb. A series of photos are taken of the injured limb. If the bone is broken, fracture should be reduced before the photos are taken. The photogrammetric processing methods described above are then used to obtain the surface coordinates of the injured limb. In order to define common surface points on the limb, reference points can be placed on the limb. The reference points can simply be any contrasting color points, patterns, shapes, objects, symbols or other optical indicators which are easily visible. The reference points can be black or colored ink marks that are placed on the body with a pen. In other embodiments, the reference points can be lights such as visible light, infrared light, points or grids, stickers or objects or any other visible point of reference. For example, circular adhesive stickers which have a contrasting color can be placed on the patient and photographed. The stickers can provide accurate reference points which can be used to produce the digital representation of the patient's limb and/or body. In the preferred embodiment, the reference points are placed and evenly distributed around the entire limb or portion of the body that the brace is being constructed for.

Figure 42:
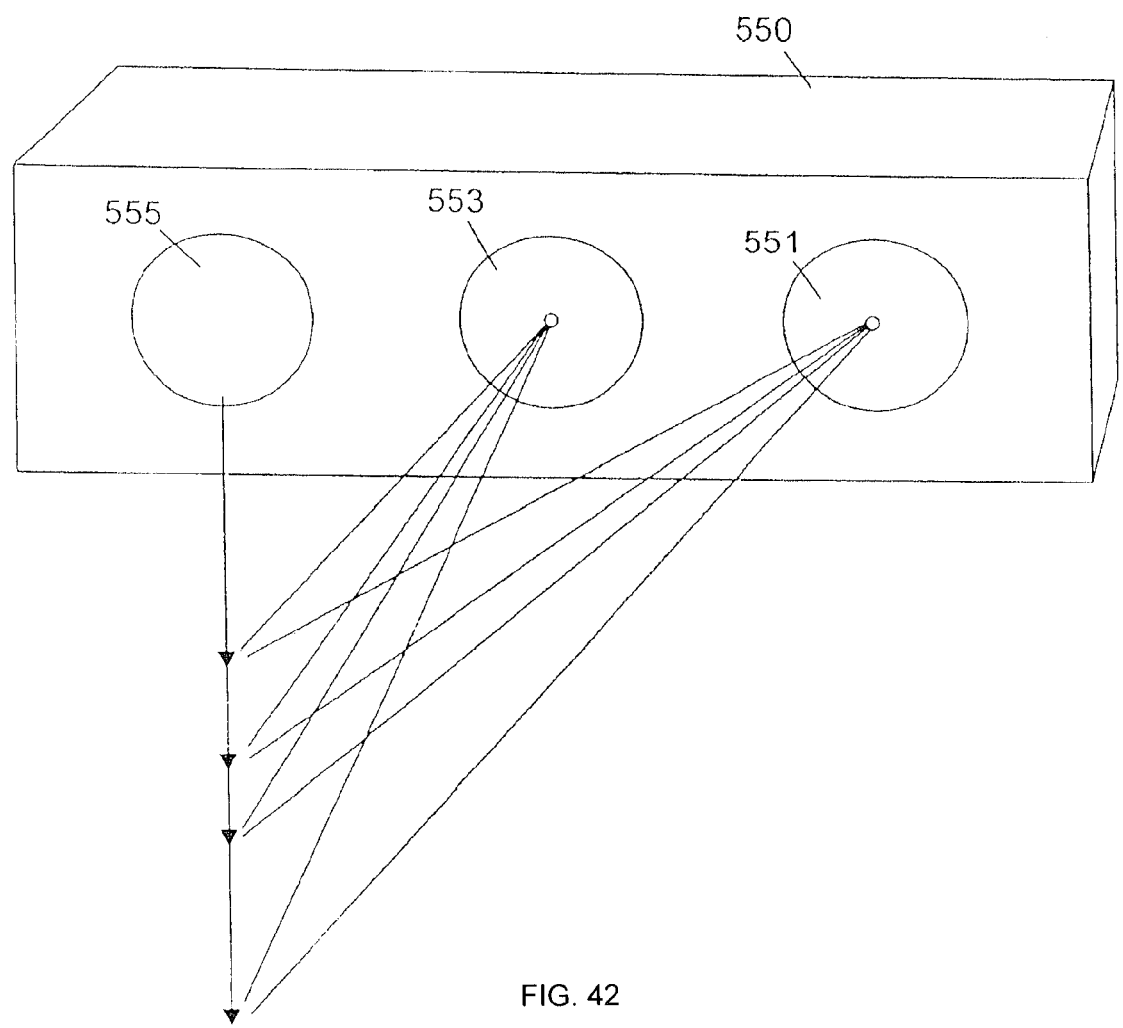

With reference to FIG. 42, in an embodiment the three dimensional surface data of a patient can be obtained using an optical device comprising a color image camera 551, an infrared (IR) camera 553 and an infrared (IR) light source 555 coupled to a signal processor. The IR light source 555, IR camera 553 and color image camera 551 can all be mounted on one side of the optical device 550 so that the color camera 551 and IR camera 553 have substantially the same field of view and the IR light source 551 projects light within this same field of view. The IR light source 555, IR camera 553 and color image camera 551 can be mounted at fixed and known distances from each other on the optical device 550. The color image camera 551 can provide color information for the patient's limb 560 or portion of the patient within the viewing region of the camera 551. The IR camera 553 and IR light source 555 can provide distance information for each area of the patient's limb 560 exposed to the IR light source 555 that is within the viewing region of the IR camera 553. The infrared light source 555 can include an infrared laser diode and a diffuser. The laser diode can direct an infrared light beam at the diffuser causing a pseudo random speckle or structured light pattern to be projected onto the patient's limb 560. The diffuser can be a diffraction grating which can be a computer-generated hologram (CGH) with a specific periodic structure. The IR camera 553 sensor can be a CMOS detector with a band-pass filter centered at the IR laser wavelength. In an embodiment, the color image camera 551 can also detect the IR light projected onto the patient's limb 560.

Figure 43:
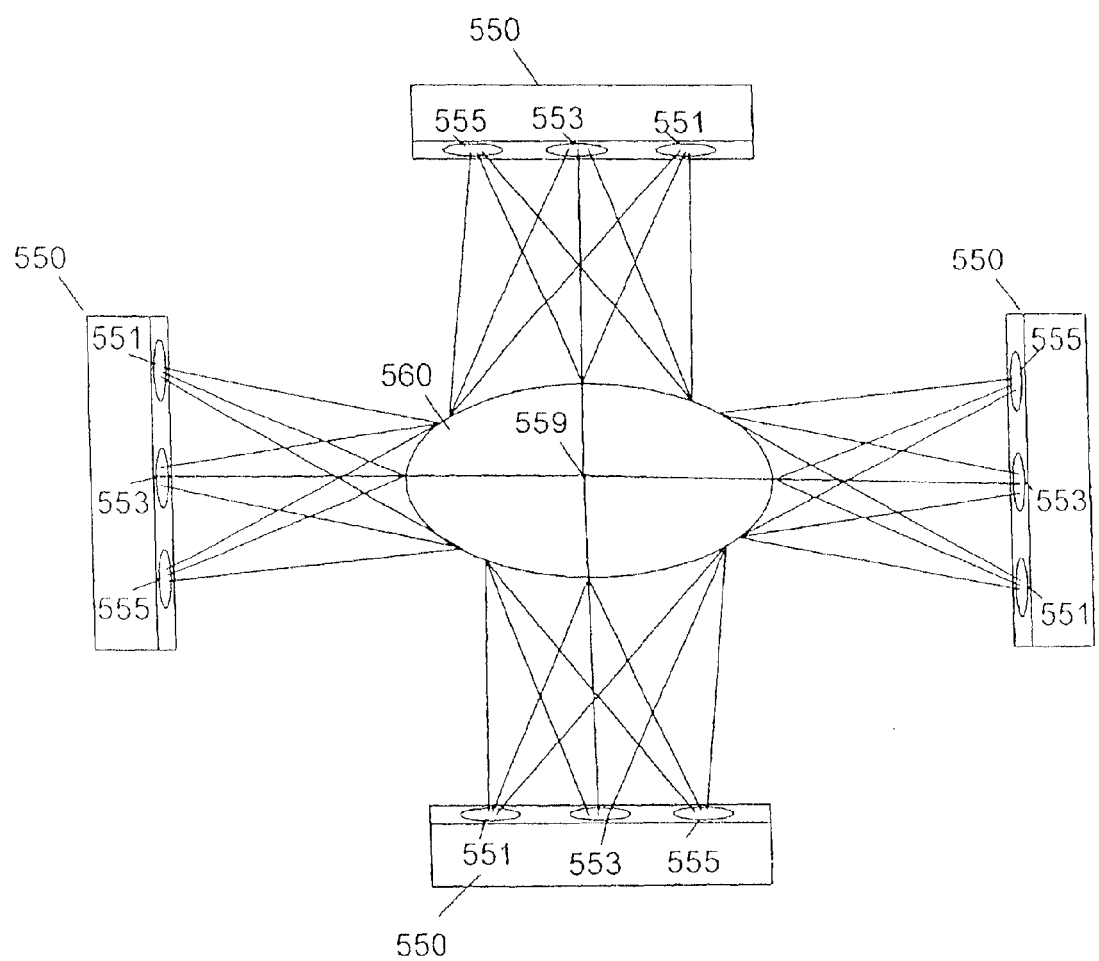

With reference to FIG. 43, the optical device 550 can detect the distance between the infrared camera 553 and the IR light on the patient because the camera 553 sees the patient's limb at a different angle than the infrared light source 555 and the distance between infrared light source 555 and IR camera 553 is defined. The principle of structured light distance sensing is that given a specific angle between IR light source 555 and IR sensor 553 for each point of light on the patient's limb and a distance between the object and the IR light source 555 or IR camera 553 or color camera 551 can be determined by triangulation. The angles of the light points on the patient's limb detected by the IR camera 553 and the color camera 551 will change depending upon the distance of the patient from the optical device 550. In an embodiment, a calibration process can be used to determine the angles of each light point on a plane at different distances from the optical device 550. By knowing the angles and corresponding distances for each point of IR light and distance of the points of light from the optical device 550 can be determined. These distance calculations for an object can also be known as three dimensional mapping. The distance value for each light point can also be matched with the visible color image data so that color and distance information for each pixel of a patient image can be determined and stored.

Because a single picture can capture the patient in a fixed position, the IR light source 555 can be project the IR light on the patient and the IR camera 553 can take a single photograph of the patient 560. The color camera 551 may also simultaneously take a single photograph of the patient's limb 560. In other embodiments, multiple IR or color photographic images can be taken of the patient's limb 560 in different positions and the corresponding image shifts are directly relates to distance from the camera. Each successive photographic image is served as a reference photograph for the next frame calculation so that the movement of the patient can be detected and the changes in the three dimensional mapping can be recorded.

Figure 44:
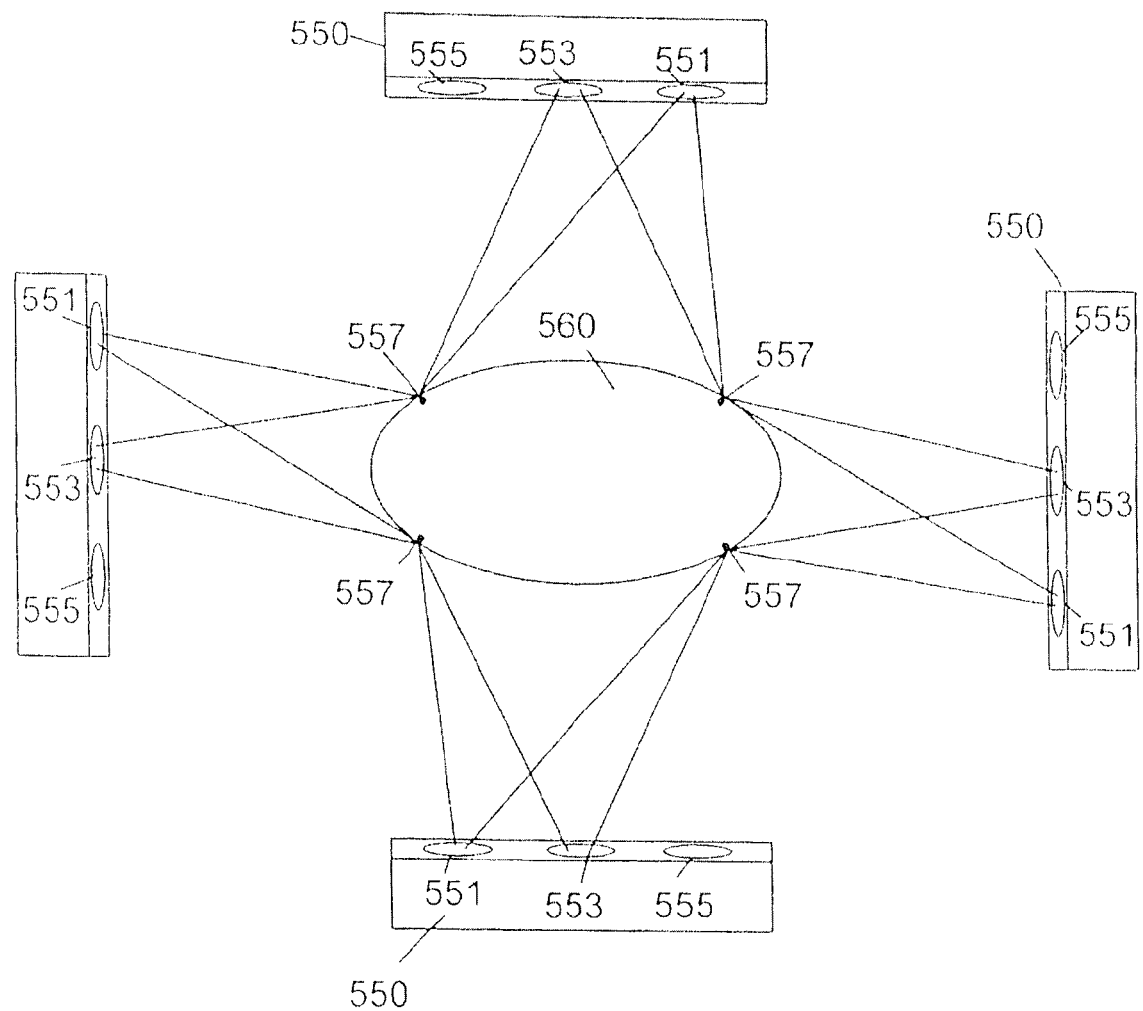

As discussed, the IR camera can detect the light pattern projected onto the patient's limb and through triangulation, the distance between the IR camera and color camera and each point of the light pattern on the patient can be determined. However, the distance information for the points can only determine a three dimensional surface of the patient's limb or a portion of the patient's limb that are detected by the IR camera 553 or the color camera 551. With reference to FIG. 44, in order to determine a three dimensional surface around a patient's limb, multiple optical devices 550 can be placed around the patient and the three dimensional surface information from each of these cameras can be combined to determine the three dimensional surfaces around a circumference of a patient's limb. In an embodiment the IR light from each of the IR light sources 555 can be emitted simultaneously and the photographs from all of the IR cameras 553 and color cameras 551 can be taken simultaneously. In other embodiments, the IR light sources 555 can interfere with the IR cameras 553 that are not part of the same optical system 550. Rather than protecting IR light from all of the IR light sources 555 at the same time, the optical systems 550 can be configured to sequentially illuminate with IR light and photograph the patient's limb 560. A first optical system 550 will emit the IR light and take IR and color photos of the patient's limb 560. The first optical system 550 can then stop projecting IR light onto the patient's limb 560 and the second optical system 550 can then emit the IR light, take IR and color photos of the patient's limb 560. The second optical system 550 can then stop projecting IR light onto the patient's limb 560. This described process can be sequentially repeated for the remaining optical systems 550.

After taking the IR photographs, surface data for different sides of the patient's limb 560 can be combined from the optical systems 550 in various different ways. For example, the multiple IR cameras 553 can produce distance information for the photographed patient's limb 560 that can be combined using a photogrammetry process to determine a full or partial circumferential three dimensional representation of the patient's limb 560. The surface data from the optical systems 550 will include some of the same surface areas of the patient's limb 560 that were also captured by at least two of the adjacent optical system 550. Because the three dimensional shape data is the same, the system can identify these matching surface shapes and combine the surface data to obtain continuous surface data for the photographed portion of the patient's limb 560. In an embodiment, the optical systems 550 can be aligned around the patient 560 with the IR cameras 553 radially aligned in a planar manner and directed towards a center point 559 within a cross section of the patient's limb 560. The optical systems 550 can each produce surface data for a portion of the patient's limb 560. Because the IR photos are taken on a common plane, the surface data from the different optical systems 550 can be joined by determining the distance of the surface data from the center point 559. In an embodiment, a first set of calibration IR and/or color photographs can be taken by the optical systems 550 of a physical center point marker 559 without the patient's limb 560. IR and/or color photos can then be taken of the patient 560. From this information, the position of the center point 559 relative to the surface data of the patient 560 can be determined. By knowing the distances and alignment of the surface data to a common center point 559, the surface data from the different optical systems 550 can be combined. In an embodiment, the optical systems 550 can be arranged on direct opposite sides of the patient's limb 560. Although four optical systems 550 are shown, in other embodiments, two or more optical systems 550 can be used to obtain the surface data for the patient's limb 560. Three optical systems 550 may be required to have some overlapping surface data for the patient's limb 560.

Figure 45:
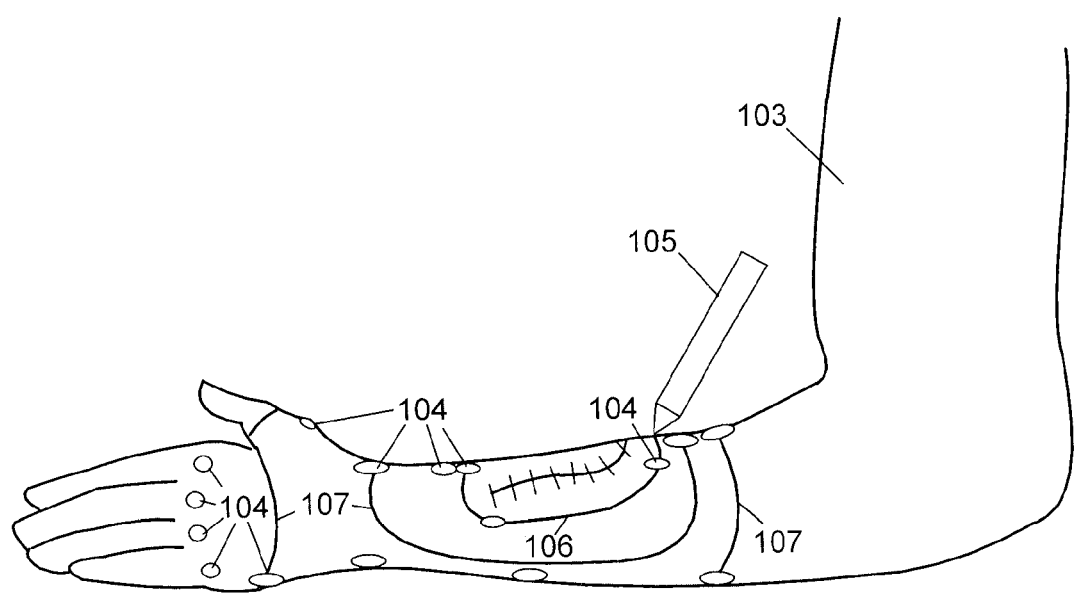
FIG. 45 illustrates a marked patient for detection by the photographic detection system.

With reference to FIG. 45, in other embodiments the surface data from the optical systems 550 can be combined by using alignment markings 557 on the patient's limb 560. The patient's limb 560 may be covered with a material and a visible or IR marking 557 can be projected onto the patient's limb 560 at locations that are within the field of view of two or more optical systems 550. The color camera 551 may detect both visible and IR markings and the IR camera 553 may only detect IR markings. The optical systems can be able to distinguish the IR light from the IR markings because the shape of the IR marking 557 can be larger or may have a different shape. The surface data from adjacent optical systems 550 can be combined by using a photogrammetry or image correlation process that matches the positions of the markings 557 that are photographed by both optical systems 550.

Figure 46:
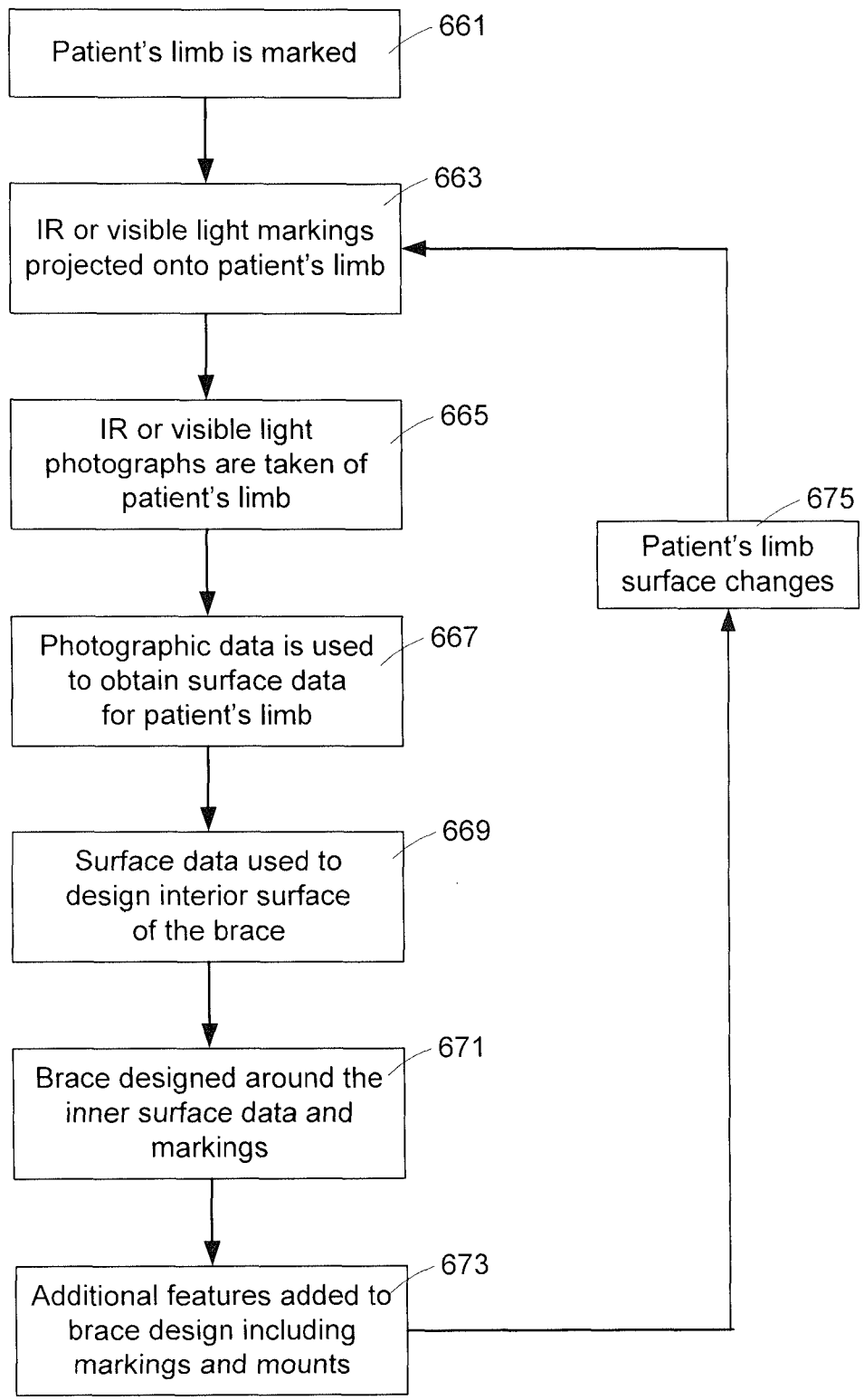
FIG. 46 illustrates a flow chart for fabricating a brace.

In addition to the reference points, the patient can also be marked to define an edge of the brace, a seam of a modular brace or other features. With reference to FIG. 46, the doctor can mark the patient's arm 103 with a pen 105 or with stickers to define the locations of the edge of the brace or other important features. The edge or seam marking can be one or more continuous ink lines 107 that extend around the patient's arm 103. In other embodiments, the edge or seam can be defined by a series of ink marks that define the edge of the brace and are connected during the brace design. Additional ink lines 109 can also be marked on the patient to create edges for the brace pieces. In other embodiments, other marking devices such as stickers can be placed on the patient rather than ink to indicate areas of interest or brace design on the patient.

For example, the patient may have injured areas from an operation that has been closed with stitches and should not be in contact with the rigid brace. By providing an opening in the brace, the patient's stitches will not be pressed against the brace structure. In FIG. 46, the doctor has drawn a circle around or place stickers around or on this portion of the patient's body so that the brace can be designed around this area. The doctor can also make notes on the patient's arm 103. For example, the doctor can write information indicating the location of the injury as well as information indicating the locations of bones, joints, tendons and ligaments. These anatomical locations are important in the design of the brace and are therefore marked on the patient's arm 103. Because photogrammetry uses photographs, the digital pictures will record all of the stickers, ink lines, other ink markings.

In addition to being the proper dimensions, the brace must also be strong enough for the required use. An ankle brace or walking brace may be required to support the user's weight and impact while running or jumping and an arm brace must be able to withstand the normal use forces. In an embodiment, the strength of the brace is determined by the geometry of the brace and the materials used to fabricate the brace. Suitable materials include high strength plastics such as high strength polyamides metals, alloys and composites such as carbon fiber in an epoxy binder.

Figure 47:
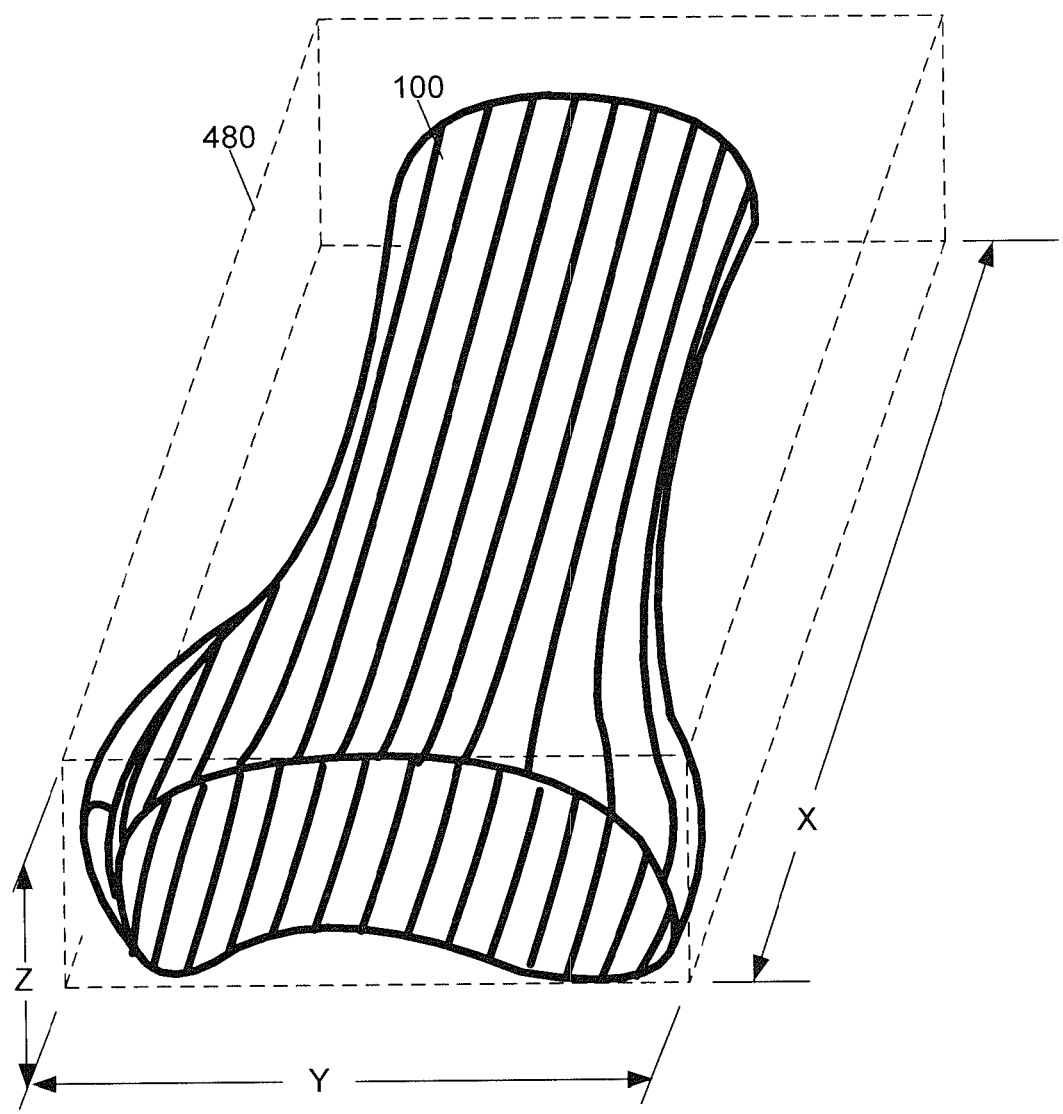
FIG. 47 illustrates an embodiment of the brace design data in a virtual box prior to fabrication with a three dimensional printer.

With reference to FIG. 47, a flowchart of the process steps for fabricating a brace is illustrated. As discussed above, the patient's limb can be marked 661 with any type of marking device such as a sticker or ink that can be photographed. The markings can indicate a surface location, the location of the injury, edges of the brace, seams of the modular brace, seams of the brace pieces, sensitive areas, locations of stitches, and other body features. The patient's limb can be illuminated with IR or visible light in a pattern such as dots, lines, grids or any other plurality of light points 663. The limb can be photographed with IR and/or visible light cameras as described 665. From the photographic data, the surface data for the patient's limb can be obtained 667. In other embodiments the limb may not be illuminated with an IR or visible light pattern and the surface data can be obtained by the natural markings on the patient's skin.

The surface data can be used to design interior surfaces of a brace 669. With the limb surface data and additional information about the limb injury, the brace can be designed to prevent specific types of movements and avoid contact with specific areas of the limb 671. The brace design can also be modified to include additional marking and mounting features 673. The markings added to the brace design can include information, ornamental designs, injury locations, etc. The mounts added to the brace can include device mounts and instrumentation mounts. If the limb changes in size but remains injured, a new brace may need to be fabricated to provide the required support and restricted movement 675. The described process can be repeated to fabricate a new brace based upon new photographs of the patient's limb.

After the brace or device is designed with the adjustable couplings incorporated, the brace design data is transmitted to a three dimensional fabrication machine that constructs the brace. In an embodiment, the three dimensional fabrication machine is rapid prototyping, rapid manufacturing, layered manufacturing, 3D printing, laser sintering, and electron beam melting (EBM), fused material deposition (FDM), CNC, etc. The fabrication machine produces a three dimensional single or multiple piece structure that can be plastic, metal or a mix of different materials by forming planar cross section layers of the structure on a previously formed planar cross section layers. This layered fabrication process is continued from one end of the structure to the opposite end until the structure is completely fabricated.

In order to efficiently produce the described devices, it can be desirable to simultaneously produce as many component parts as possible. Many fabrication machines can produce parts fitting within a specific volume in a predetermined period of time. For example, a brace can fit around the torso of a patient and have a large space in the center. This brace can be made, but it will only make one device. In order to improve the efficiency, the brace can be designed as multiple pieces that are later coupled or fused together. Rather than making a single brace with the large open center area, the described fabrication methods can be used to simultaneously produce components for two or more braces that occupy the same specific volume as a single piece brace. The cost of fabrication using a three dimensional fabrication machine can be proportional to the amount of time required to print the components rather than the raw material costs. The print time can be minimized by placing as many component cross sections into the print area as possible. If a back or limb brace normally has a large open center area the print cost efficiency can be poor. However, if the brace is a modular design, the modular section pieces can be fabricated in a more efficient manner. For example, multiple modular section pieces can be fabricated simultaneously with the convex surfaces of a first section piece adjacent to concave surfaces of another section piece. By laying out the components in an efficient production manner for fabrication by an additive material machine, the cost of fabrication can be significantly reduced. The components can then be assembled and coupled or fused together to form the brace. In an embodiment, the inner surface of the brace can be manufactured with a high resolution so that the inner surface is very smooth.

When the brace is fabricated using a three dimensional printing machine, the brace is formed by depositing a plurality of parallel planar layers of material with each layer fused to the adjacent layer. Each layer of material used to form the brace can have a predetermined and uniform thickness. In order to optimize the efficiency of the brace fabrication, it can be desirable to minimize the number of parallel planar layers used to create the brace. This minimizes the number of layers that are formed to create the brace and optimizes the fabrication efficiency. In an embodiment, the brace design information can be placed in a virtual box having square corners. The parallel planar layers formed to create the brace can be perpendicular to the shortest dimension of the brace which can be the thickness of the box.

For example, with reference to FIG. 48, a brace 100 is illustrated in a virtual box 480 having square corners and planar sides. The brace 100 can be an elongated structure that extends from the forearm to the hand and define the length axis. The length of the box 480 X can be the longest dimension of the brace 100 and a thickness of the box 480 Z can be the shortest dimension of the brace 100. In an embodiment, the parallel planar layers that are fused to form the brace 100 can be parallel to the length axis, X. In an embodiment, the parallel planar layers that are fused to form the brace 100 are substantially perpendicular to the thickness axis Z which can be the smallest overall dimension of the brace. In another embodiment, the parallel planar layers that are fused to form the brace 100 are substantially parallel to the width axis Y. In other embodiments, multiple braces 100 can be fabricated simultaneously in the same virtual box 480. By utilizing more volume within the same virtual box 480 or a similar sized virtual box, the braces 100 can be fabricated more efficiently since the time for fabrication can be directly proportional to the volume of the virtual box 480.

After the brace has been formed, additional processing can be performed on the inner surface to increase the smoothness. The inner surface can be tumbled, sanded, polished, or other processes can be used to create the smooth inner surfaces of the brace. These processes can be performed by hand or by a machine. In other embodiments, a filler material can be deposited on the inner surface of the brace shell to create a smooth surface. For example, the inner surface may be painted and the paint may fill the uneven surfaces and dry to a smooth surface. Alternatively, the inner surface can be heated to cause the brace material to reflow and create a smooth inner surface. The inner surface can have a The use of a photographic process has many advantages over other surface scanning technologies such as laser scanning. The process for transposing the locations of features from the patient to the brace or device is simplified because the doctor can apply location marks to the patient directly or on a form fitting covering. Thus, the locations of the features are much more likely to be accurately placed on the final product. The equipment costs are also reduced because the digital cameras, computers and electronic memory are inexpensive. The photographic equipment is also portable, so it can be easily transported to patient's location. The digital data can then be transmitted electronically to a fabrication machine located at a guild. Alternatively, the digital device data can be recorded onto a disk and transmitted to the fabrication machine.

The illustrated braces provide the required support and protection for the patient while minimizing all unnecessary structural components. This minimalistic design matches the patient's anatomy and provides a more comfortable fit. These braces are also lighter in weight than traditional braces and provide greater ventilation. Although, the braces are shown for hands and forearms, in other embodiments, the inventive braces can also be used for any other portion of the patient's body including elbows, feet, legs, ankles, knees, back, neck, shoulders, and other portions of the body.

The present disclosure, in various embodiments, includes components, methods, processes, systems and/or apparatus substantially as depicted and described herein, including various embodiments, subcombinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation. Rather, as the following claims reflect, inventive aspects lie in less than all features of any single foregoing disclosed embodiment.

What is claimed is:

1. A brace for supporting a limb of a patient comprising:
a brace body having an elongated shape that defines an axis, a proximal end and a distal end, the brace body having an inner surface that conforms to the limb of the patient and an outer surface; and
elongated fenestrations formed in the brace body, each of the elongated fenestration having a length that is longer than a width and the lengths of the elongated fenestrations are substantially aligned with the axis of the brace body, the fenestrations each have two sides defined by two straight beams when the brace is in a normal contracted state and two ends defined by two posts, the fenestrations are substantially parallel to each other and offset with the posts coupled to mid sections of the adjacent fenestrations;
wherein the brace is a single piece integrated structure that is radially elastic and expands radially with the two straight beams elastically bent in a zigzag manner and the fenestrations in elongated diamond shapes when the brace is in an expanded state and wherein the brace is adapted to prevent bending of the limb and is adapted to be worn on the limb without any compressible padding.

2. The brace of claim 1 further comprising:
a first edge that extends from the inner surface to the outer surface and along a side of the brace body from the proximal end of the brace body to the distal end; and
a second edge that is adjacent to the first edge and that extends from the inner surface to the outer surface and along the side of the brace body from the proximal end of the brace body to the distal end.

3. The brace of claim 2 further comprising a coupling for releasably holding the first edge adjacent to the second edge.

4. The brace of claim 2 wherein the limb is a forearm and at least portions of the first edge and the second edge are adjacent to an ulnar border of the forearm.

5. The brace of claim 1 further comprising a wrap that is releasably coupled around the circumference of the brace.

6. The brace of claim 1 wherein the length of the elongated fenestrations is greater than 1 inch and widths of the elongated fenestrations is less than 0.25 inch.

7. The brace of claim 1 wherein a thickness of the brace body is greater 0.05 inch and less than 0.50 inch.

8. The brace of claim 1 wherein each of the elongated fenestrations has a width that is substantially uniform along the length.

9. The brace of claim 1 wherein the elongated fenestrations each have a proximal end and a distal end, the elongated fenestrations are aligned along the axis of the brace body with the distal end of a first of the elongated fenestrations adjacent in the axial direction to the distal end of a second of the elongated fenestrations and the distal end of the second of the elongated fenestrations adjacent in the axial direction to the distal end of a third of the elongated fenestrations.

10. The brace of claim 9 wherein the distal end of the third of the elongated fenestrations is adjacent in the axial direction to the distal end of a fourth of the elongated fenestrations.

11. The brace of claim 1 wherein the elongated fenestrations each have a proximal end, a distal end and a middle section between the proximal end and the distal end, the elongated fenestrations are aligned circumferentially around the axis of the brace body with the distal end of a first of the elongated fenestrations adjacent in the circumferential direction to the middle section of a second of the elongated fenestrations and the distal end of the second of the elongated fenestrations adjacent in the circumferential direction to the middle section of a third of the elongated fenestrations.

12. The brace of claim 11 wherein the distal end of the third of the elongated fenestrations is adjacent in the circumferential direction to the middle section of a fourth of the elongated fenestrations.

13. The brace of claim 1 wherein the brace is placed around the limb to prevent axial bending of the limb.

14. The brace of claim 1 wherein the brace is placed around the limb and the brace allows radial expansion of the limb.

15. A brace for supporting an arm of a patient, the arm having a hand, a wrist and a forearm, the brace comprising:
a brace body having an elongated shape that defines an axis, a proximal end and a distal end, the brace body having an inner surface that conforms to the arm of the patient and an outer surface; and
elongated fenestrations formed in the brace body, each of the elongated fenestration having a length that is longer than a width and the lengths of the elongated fenestrations are substantially aligned with the axis of the brace body, the fenestrations each have two sides defined by two straight beams when the brace is in a normal contracted state and two ends defined by two posts, the fenestrations are substantially parallel to each other and offset with the posts coupled to mid sections of the adjacent fenestrations;
wherein the brace is a single piece integrated structure that is radially elastic and expands radially with the two straight beams elastically bent in a zigzag manner and the fenestrations in elongated diamond shapes when the brace is in an expanded state and wherein the brace is adapted to prevent bending of the limb and is adapted to be worn on the limb without any compressible padding.

16. The brace of claim 15 wherein an edge of the distal limb support is adjacent to a palmar digital crease of the hand.

17. The brace of claim 15 wherein an edge of the distal limb support does not extend over proximal phalanx segments of the fingers.

18. The brace of claim 15 wherein the distal limb support surrounds a palm portion of the hand.

19. The brace of claim 15 wherein the distal limb support surrounds a thenar portion of the hand.

20. The brace of claim 15 wherein the interior surface of the brace at the distal limb support has a convex surface that is adjacent to a palmar surface of the hand.

21. The brace of claim 15 wherein the brace prevents palmar flexion movement of the hand.

22. The brace of claim 15 wherein the brace allows rotational movement of the hand about a center axis of the brace relative to the forearm.

* * * * *